US009771348B2

(12) United States Patent
Kwak et al.

(10) Patent No.: US 9,771,348 B2
(45) Date of Patent: Sep. 26, 2017

(54) METHOD FOR PREPARING BENZAMIDE DERIVATIVE, NOVEL INTERMEDIATE USED IN PREPARATION OF BENZAMIDE, AND METHOD FOR PREPARING NOVEL INTERMEDIATE

(71) Applicant: DONG-A ST CO., LTD, Seoul (KR)

(72) Inventors: Woo Young Kwak, Gyeonggi-do (KR); Kyung Seok Lee, Gyeonggi-do (KR); Ullapu Punna Reddy, Gyeonggi-do (KR); Soon Kyu Jung, Gyeonggi-do (KR); Tae Sun Park, Gyeonggi-do (KR); Joong In Lim, Gyeonggi-do (KR)

(73) Assignee: DONG-A ST CO., LTD, Seoul (KR)

( * ) Notice: Subject to any disclaimer, the term of this patent is extended or adjusted under 35 U.S.C. 154(b) by 0 days.

(21) Appl. No.: 14/907,267

(22) PCT Filed: Jul. 11, 2014

(86) PCT No.: PCT/KR2014/006282
§ 371 (c)(1),
(2) Date: Jan. 22, 2016

(87) PCT Pub. No.: WO2015/012515
PCT Pub. Date: Jan. 29, 2015

(65) Prior Publication Data
US 2016/0185751 A1 Jun. 30, 2016

(30) Foreign Application Priority Data
Jul. 25, 2013 (KR) .................. 10-2013-0087992

(51) Int. Cl.
*C07D 401/06* (2006.01)
*C07C 55/14* (2006.01)
*C07C 57/145* (2006.01)
*C07C 57/15* (2006.01)
*C07C 59/255* (2006.01)
*C07C 59/265* (2006.01)

(52) U.S. Cl.
CPC ............ *C07D 401/06* (2013.01); *C07C 55/14* (2013.01); *C07C 57/145* (2013.01); *C07C 57/15* (2013.01); *C07C 59/255* (2013.01); *C07C 59/265* (2013.01)

(58) Field of Classification Search
CPC .................................................. C07D 401/06
USPC ........................................................ 546/210
See application file for complete search history.

(56) References Cited

U.S. PATENT DOCUMENTS

| | | | |
|---|---|---|---|
| 4,138,492 A | 2/1979 | Noverola et al. | 424/267 |
| 4,962,115 A | 10/1990 | Van Daele | 514/326 |
| 5,057,525 A | 10/1991 | Van Daele | 514/318 |
| 5,137,896 A | 8/1992 | Van Daele | 514/327 |
| 5,864,039 A * | 1/1999 | Kawakita | C07D 265/14 544/111 |
| 6,352,999 B1 | 3/2002 | Kennis et al. | 514/291 |
| 6,495,685 B1 | 12/2002 | Maeda et al. | 544/242 |
| 9,221,790 B2 * | 12/2015 | Kim | C07D 401/06 514/326 |
| 9,346,840 B2 * | 5/2016 | Johnson | C07D 401/04 546/208 |
| 2008/0312213 A1 | 12/2008 | Hamprecht et al. | 514/217.01 |
| 2010/0093801 A1 | 4/2010 | Chung et al. | 514/331 |
| 2010/0105727 A1 | 4/2010 | Yoo et al. | 548/400 |
| 2013/0085160 A1 | 4/2013 | Kim et al. | 514/229 |
| 2013/0296571 A1 | 11/2013 | Son et al. | 546/75 |
| 2013/0317052 A1 | 11/2013 | Son et al. | 514/289 |
| 2014/0155609 A9 | 6/2014 | Son et al. | 546/75 |

FOREIGN PATENT DOCUMENTS

| | | |
|---|---|---|
| EP | 0 774 460 | 5/1997 |
| JP | 2002-509856 A | 4/2002 |
| JP | 2002-526547 A | 8/2002 |
| JP | 2008-503524 A | 2/2008 |
| JP | 2009-167166 A | 7/2009 |
| KR | 10-2011-0118446 | 10/2011 |
| WO | WO 99/02494 | 1/1999 |
| WO | WO 99/20627 | 4/1999 |
| WO | WO 00/31033 | 6/2000 |
| WO | WO 2008/089005 | 7/2008 |
| WO | WO 2008/114971 | 9/2008 |
| WO | WO 2011/132901 | 10/2011 |

OTHER PUBLICATIONS

Brenton et al. "Base-promoted . . . " J. Org. Chem. 69, p. 1720-22 (2004).*
Greene "Protective groups . . . " p. 218-220, 224, 251 (1982).*
Kawakita et al. "Preparation of 5-HT4 . . . " CAreact 130:153575 (1999).*
Kim et al. "N-piperidin-4-yl . . . " CAreact 155:562760 (2011).*
Wijtmans et al. "Triazole ligands . . . " J. Me. Chem. 54, 1693-1703 (2011).*
Deprotecting groups, Wikipedia, p. 1-14 (2016).*
Letter/Written Disclosure of the Information Disclosure Statement for the above-referenced application, filed herewith on Apr. 21, 2016, 2 pages.

(Continued)

Primary Examiner — Celia Chang
(74) Attorney, Agent, or Firm — Dentons US LLP; Stephanie Seidman

(57) ABSTRACT

The present invention relates to a method for preparing N-[[1-{3-(1,2,3-triazol-1-yl)propyl}piperidin-4-yl]methyl]-4-amino-5-chloro-2-methoxybenzamide, which is a novel benzamide derivative as a 5-HT4 receptor agonist, or a pharmaceutically acceptable salt thereof; to a novel intermediate capable of being used in the preparation of the compounds; and to a method for preparing the same. The preparation methods of the present invention can be useful for mass production since a low-priced reagent and intermediate are used and the number of reaction processes is decreased, thereby saving preparation costs and improving the yield.

22 Claims, No Drawings

(56) References Cited

OTHER PUBLICATIONS

Bockaert et al., "5-HT 4 Receptors," CNS Drugs, 1:6-15 (1994).
Bockaert et al., "The 5-HT 4 Receptor: a place in the sun," Trends in Pharmacol. Sci., 13:141-145 (1992).
Bylov et al., "Synthesis and anti-inflammatory activity of N-substituted 2-oxo-2H-1-benzopyran-3-carboxamides and their 2-iminoanalogues," Eur. J. Med. Chem. 34:997-1001 (1999).
CALPUS Accession No. 2000:466896, American Society for Pharmacology and Experimental Therapeutics (2000).
Claeysen et al., "Pharmacological Properties of 5-Hydroxytryptamine$_4$ Receptor Antagonists on Constitutively Active Wild-Type and Mutated Receptors," Molecular Pharmacology 58(1):136-144 (2000).
Eglen et al., "Central 5-HT$_4$ Receptors," Trends in Pharmacol. Sci., 16:391-398 (1995).
Ford et al., "The 5-HT$_4$ Receptor," Med. Res. Rev., 13:633-662 (1993).
Gilchrist, "Heterocyclic Chemistry" Addison Wesley Longman, 1997, pp. 26-29.
Gullikson et al., "Gastrointestinal Motility Responses to the S and R Enantiomers of Zacopride, a 5-HT4 Agonist and 5-HT3 Antagonist," Drug Dev. Res., 26:405-417 (1992).
Itoh et al., "Synthesis and pharmacological evaluation of carboxamide derivatives as selective serotoninergic 5-HT$_4$ receptor agonists," Eur. J. Med. Chem. 34:329-341 (1999).
Iwanaga et al., "Stimulatory Effect of N-[4-[2-(Dimethylamino)ethoxy]benzyl]-3,4-Dimethoxybenzamide Hydrochloride (HSR-803) on Normal and Delayed Gastrointestinal Propulsion," Jpn J Pharmacol. 56:261-269 (1991).
Kaumann et al., "A 5-HT$_4$-like receptor in human right atrium," Naunyn-Schmiedeberg's Arch Pharmacol 344:150-159 (1991).
Romanelli et al., "Synthesis and Biological Activity of a Series of Aryl Tropanyl Esters and Amides Chemically Related to 1H-Indole-3-carboxylic Acid endo 8-Methyl-8-azabicyclo[3.2.1] oct-3-yl Ester," Arzheim Forsch./Drug Res. 43: 913-918 (1993).

Silverman, R. "The Organic Chemistry of Drug Design and Drug Action," Elsevier, 2004, pp. 29-32.
Sonda et al., "Design and Synthesis of Orally Active Benzamide Derivatives as Potent Serotonin 4 Receptor Agonist," Bioorganic & Medicinal Chemistry 11:4225-4234 (2003).
Sonda et al., "Synthesis and pharmacological evaluation of benzamide derivatives as selective 5-HT$_4$ receptor agonists," Bioorganic & Medicinal Chemistry 13:3295-3308 (2005).
Wyngaert et al., "Cloning and expression of a human serotonin 5-HT$_4$ receptor cDNA." J Neurochem. 69:1810-1819 (1997).
International Search Report and Written Opinion, issued Oct. 31, 2014, in connection with International Patent Application No. PCT/KR2014/006282 [English Translation], 10 pages.
International Preliminary Report on Patentability, issued on Jan. 26, 2016, in connection with International Patent Application No. PCT/KR2014/006282 [English Translation], 6 pages.
U.S. Appl. No. 14/003,077, filed Oct. 3, 2013.
U.S. Appl. No. 14/003,087, filed Oct. 3, 2013.
U.S. Appl. No. 14/765,318, filed Jul. 31, 2015.
U.S. Appl. No. 14/392,160, filed Dec. 23, 2015.
Letter/Written Disclosure of the Information Disclosure Statement for the above-referenced application, filed herewith on Dec. 28, 2016, 3 pages.
Taylor et al., "6.11 N-Acylation Reactions of Amines," in "Comprehensive Organic Synthesis II," Elsevier, pp. 427-478 (2014).
Valeur et al., "Amide bond formation: beyond the myth of coupling reagents," Chemical Society Reviews 38(2):606-631 (2009).
Extended European Search Report, dated Dec. 1, 2016, in connection with corresponding European Patent Application No. 14829058.8, 7 pages.
Letter/Written Disclosure of the Supplemental Information Disclosure Statement for the above-referenced application, filed herewith on Jan. 17, 2017, 3 pages.
Gonda et al., "Efficient Synthesis of deuterated 1,2,3-triazoles." Tetrahedron Letters 51:6275-6277 (2010).
Office Action, mailed Dec. 20, 2016, in connection with corresponding Japanese Patent Application No. 529701/2016 [English translation and original document in Japanese], 11 pages.

* cited by examiner

METHOD FOR PREPARING BENZAMIDE DERIVATIVE, NOVEL INTERMEDIATE USED IN PREPARATION OF BENZAMIDE, AND METHOD FOR PREPARING NOVEL INTERMEDIATE

RELATED APPLICATIONS

This application is the U.S. National Stage of International Application. No. PCT/KR2014/006282, filed 11 Jul. 2014, which claims benefit of priority to Korean Patent Application KR 10-2013-0087992, filed 25 Jul. 2013, the specification of which is incorporated by reference herein.

BACKGROUND

Technical Field

The present disclosure relates to a method for preparing N-[[1-{3-(1,2,3-triazol-1-yl)propyl}piperidin-4-yl]methyl]-4-amino-5-chloro-2-methoxybenzamide, which is a benzamide derivative, or a pharmaceutically acceptable salt thereof; to an intermediate capable of being used in the preparation of the compounds; and to a method for preparing the intermediate.

Background Art

Serotonin (5-HT) is a neurotransmitter that is widely distributed throughout the body. Serotonin receptors have been known to 7 subtypes up to date, and there has been great interest in identifying 5-HT4 receptor, which is one of the 7 subtypes, and ascertaining pharmacological actions of 5-HT4 receptor. In general, 5-HT4 receptor agonist is found to be useful in treating various diseases such as gastroesophageal reflux disease, gastrointestinal disease, gastric motility disorder, non-ulcer dyspepsia, functional dyspepsia, irritable bowel syndrome (IBS), constipation, indigestion, esophagitis, gastroesophageal disease, motion sickness, central nervous system disease, Alzheimer's disease, cognitive disorder, emesis, migraine, neurological disease, pain, cardiovascular disorders, cardiac failure, cardiac arrhythmia, diabetes and apnea syndrome. (Tips, 1992, 13, 141; Ford A. P. D. W. et al., Med. Res. Rev., 1993, 13. 633; Gullikson G. W. et al., Drug Dev. Res., 1992, 26, 405; Richard M. Eglen et al., Tips, 1995, 16, 391; Bockaert J. et al., CNS Drugs, 1, 6; Romanelli M. N. et al., Arzheim Forsch./Drug Res., 1993, 43, 913; Kaumann A. et al., Naunyn-Schmiedeberg's. 1991, 344, 150; and Romanelli M, N. et al., Arzheim Forsch./Frug Res., 1993, 43, 913). Although 5-HT4 receptor agonist could be used extensively, barely any 5-HT4 receptor agonist compounds are being used in clinical stage. Therefore 5-HT4 receptor agonist that exhibits superior effects while having minimum side-effects has been required.

Benzamide derivatives have several superior pharmacological actions. Superior pharmacological actions of the benzamide derivatives are due to its action on nervous system that is controlled by serotonin, which is a neurotransmitter. The role of serotonin, that is pharmacological actions of benzamide derivatives, has been widely involved in various diseases for several years. Furthermore, researches have been focused on production and storage regions of serotonin as well as on defining relationship between location of serotonin receptor in human body and various disease statuses or diseases. Cisapride, that is a representative 5-HT4 receptor agonist, is one of benzamide derivatives. U.S. Pat. No. 4,962,115, U.S. Pat. No. 5,057,525 and U.S. Pat. No. 5,137,896 disclose N-(3-hydroxy-4-piperidinyl) benzamide comprising cisapride. These compounds are known to stimulate gastrointestinal motility. U.S. Pat. No. 5,864,039 and KR Patent No. 10-1180174 also disclose benzamide derivatives.

As explained above, the need for methods of economically and massively synthesizing benzamide derivatives having superior usability is increasing. Therefore, methods for preparing benzamide derivatives through fewer processing steps than conventional methods, which have improved yield and superior purity, are required.

The present inventors secured a method for preparing benzamide derivatives in high yield and purity wherein production of related compounds were markedly reduced compared to the conventional methods and the processing steps is minimized by using a novel intermediate, and completed the present disclosure upon confirmation of its applicability to a large-scale production.

PRIOR ART REFERENCE

Patent Reference (Patent Reference 1) U.S. Pat. No. 4,962,115
(Patent Reference 2) U.S. Pat. No. 5,057,525
(Patent Reference 3) U.S. Pat. No. 5,137,896
(Patent Reference 4) U.S. Pat. No. 5,864,039
(Patent Reference 5) KR Patent No. 10-1180174

Non-Patent Reference (Non-Patent Reference 1) Tips, 1992, 13, 141;
(Non-Patent Reference 2) Med. Res. Rev., 1993, 13. 633
(Non-Patent Reference 3) Drug Dev. Res., 1992, 26, 405
(Non-Patent Reference 4) Tips, 1995, 16, 391
(Non-Patent Reference 5) CNS Drugs, 1, 6
(Non-Patent Reference 6) Drug Res., 1993, 43, 913
(Non-Patent Reference 7) Naunyn-Schmiedeberg's. 1991, 344, 150
(Non-Patent Reference 8) Frug Res., 1993, 43, 913

DISCLOSURE

Technical Problem

The present disclosure provides a method for preparing N-[[1-{3-(1,2,3-triazol-1-yl)propyl}piperidin-4-yl]methyl]-4-amino-5-chloro-2-methoxybenzamide, which is a benzamide derivative as a 5-HT4 receptor agonist, or a pharmaceutically acceptable salt thereof.

The present disclosure also provides a novel intermediate capable of being used in the preparation of N-[[1-{3-(1,2,3-triazol-1-yl)propyl}piperidin-4-yl]-methyl]-4-amino-5-chloro-2-methoxybenzamide, or a pharmaceutically acceptable salt thereof.

The present disclosure also provides a method for preparing the novel intermediate.

Technical Solution

The present disclosure provides a method for preparing a compound represented by Formula 3 below or a pharmaceutically acceptable salt thereof by reacting a compound represented by Formula 1 with a compound represented by Formula 2 or a pharmaceutically acceptable salt thereof.

[Formula 1]

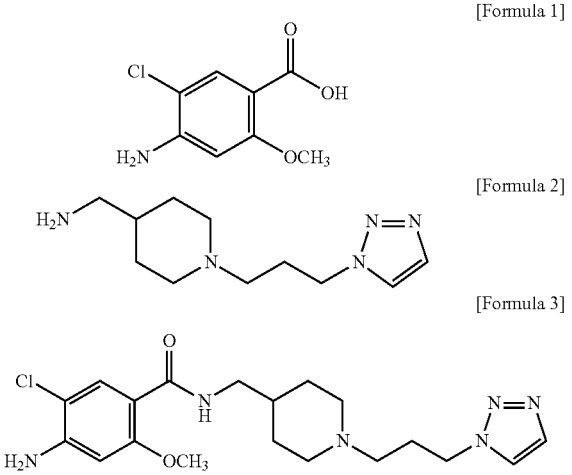

[Formula 2]

[Formula 3]

The method of the present disclosure can minimize production of related compounds when preparing the compound N-[[1-{3-(1,2,3-triazol-1-yl)propyl}piperidin-4-yl]methyl]-4-amino-5-chloro-2-methoxybenzamide, which is represented by Formula 3, or the pharmaceutically acceptable salt thereof. Therefore, the process can be simplified because there are no needs of performing a plurality of purification processes and accordingly it can be easily applied to a large-scale production.

Additionally, according to the method of the present disclosure, the compound N-[[1-{3-(1,2,3-triazol-1-yl)-propyl}piperidin-4-yl]methyl]-4-amino-5-chloro-2-methoxybenzamide represented by Formula 3, or the pharmaceutically acceptable salt thereof can be achieved in high purity and yield, reaction processes can be simplified and reaction time can be reduced compared to the conventional methods.

In the present disclosure, a reaction of the compound represented by Formula 1 with the compound represented by Formula 2 or the pharmaceutically acceptable salt thereof can be represented by Scheme 1 below.

[Scheme 1]

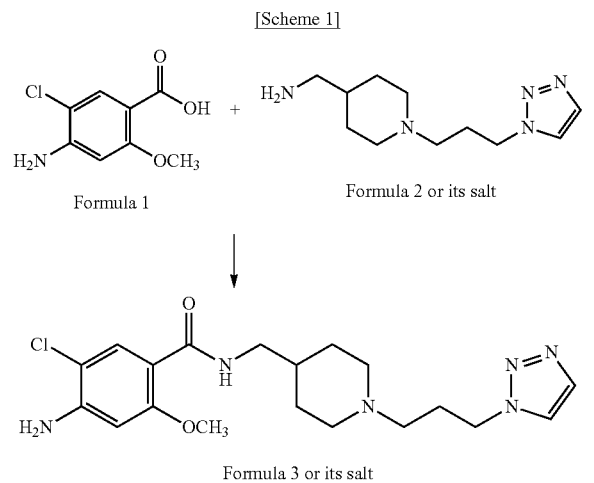 [SMILES: COc1cc(N)c(Cl)cc1C(=O)O ; NCC1CCN(CCCn2ccnn2)CC1 ; COc1cc(N)c(Cl)cc1C(=O)NCC1CCN(CCCn2ccnn2)CC1]

According to Scheme 1, the compound represented by Formula 3 or the pharmaceutically acceptable salt thereof may be prepared through a peptide bond formed between the compound represented by Formula 1 and the compound represented by Formula 2 or the pharmaceutically acceptable salt thereof.

The compound represented by Formula 1 can be synthesized via known methods or be obtained commercially.

In the present disclosure, the reaction of the compound represented by Formula 1 with the compound represented by Formula 2 or the pharmaceutically acceptable salt thereof may be conducted under existence of isobutyl chloroformate, ethyl chloroformate, carbonyldiimidazole, N-(3-dimethylaminopropyl)-N'-ethylcarbodiimide hydrochloride, 1-hydroxybenzotriazole or mixtures thereof.

In the present disclosure, the reaction of the compound represented by Formula 1 with the compound represented by Formula 2 or the pharmaceutically acceptable salt thereof may be conducted under existence of bases. The base may be a tertiary amine. The tertiary amine is not limited in its particular types. It may be N-methylmorpholine, isopropylethylamine, triethylamine, pyridine or mixtures thereof.

In the present disclosure, the reaction represented by the compound of Formula 1 with the compound represented by Formula 2 or the pharmaceutically acceptable salt thereof may be preferably preformed under both isobutyl chloroformate, ethyl chloroformate, carbonyldiimidazole, N-(3-dimethylaminopropyl)-N'-ethylcarbodiimide hydrochloride, 1-hydroxybenzotriazole or mixtures thereof, and the bases. For instance, the reaction may be performed under existence of any one selected among isobutyl chloroformate, ethyl chloroformate, carbonyldiimidazole, N-(3-dimethylaminopropyl)-N'-ethylcarbodiimide hydrochloride, 1-hydroxybenzotriazole and mixtures thereof; and the base(s) selected among N-methyl morpholine, isopropylethylamine, triethylamine, pyridine and mixtures thereof.

In the present disclosure, a type of a solvent for the reaction between the compound represented by Formula 1 and the compound represented by Formula 2 or the pharmaceutically acceptable salt thereof are not limited unless it inhibits the reaction. It may be acetonitrile, acetone, toluene, tetrahydrofuran, dichloromethane, N,N-dimethylformamide or mixtures thereof.

In the present disclosure, the reaction of the compound represented by Formula 1 with the compound represented by Formula 2 or the pharmaceutically acceptable salt thereof may be performed at about −20° C. to reflux temperature or below. Preferably, the reaction may be performed at a temperature range from about −20° C. to about 120° C., and more preferably the reaction may be performed at a temperature range from about 20° C. to about 90° C.

In the present disclosure, a type of the pharmaceutically acceptable salt are not limited in its particular types but it may be an acid addition salt formed by free acid; and the free acid may be an inorganic acid or an organic acid. The inorganic acid may be hydrochloric acid, bromic acid, sulfuric acid or phosphoric acid; and the organic acid may be oxalic acid, adipic acid, citric acid, di-p-toluoyl-L-tartaric acid, di-p-toluoyl-D-tartaric acid, citric acid, lactic acid, maleic acid, fumaric acid, gluconic acid, methanesulfonic acid, acetic acid, glycolic acid, succinic acid, L- or D-tartaric acid, tartaric acid, 4-toluenesulfonic acid, trifluoroacetic acid, galacturonic acid, embonic acid, glutamic acid or aspartic acid.

In the present disclosure, the pharmaceutically acceptable salt of the compound represented by Formula 2 may be hydrochloride, sulfate, phosphate, oxalate, adipate, citrate, di-p-toluoyl-L-tartarate, di-p-toluoyl-D-tartarate, citrate, lactate, maleate, fumarate, gluconate, methanesulfonate, acetate, glycolate, succinate, L- or D-tartarate, tartarate, 4-toluenesulfonate, trifluoroacetate, galacturonate, embonate, glutamate or aspartate. Preferably, the pharmaceutically acceptable salt of the compound represented by Formula 2 may be oxalate, succinate, adipate, tartarate, L-tartarate, D-tartarate, maleate or hydrochloride.

In the present disclosure, the pharmaceutically acceptable salt of the compound of Formula 3 may be preferably inorganic acid salt and more preferably, it may be hydrochloride.

In the present disclosure, the pharmaceutically acceptable salt of the compound represented by Formula 3 may be prepared by reacting the compound represented by Formula 3 with an acid. Types of the acid are not limited but preferably, it may be hydrochloric acid.

In the present disclosure, alcohol, ketone, ether or mixtures thereof may be used as a solvent for preparation of the pharmaceutically acceptable salt of the compound represented by Formula 3. It may be preferable for the solvent to be $C_1$-$C_5$ alcohol, $C_3$-$C_{10}$ ketone, $C_2$-$C_{10}$ ether or mixtures thereof.

In the present disclosure, the preparation of the hydrochloride of the compound represented by Formula 3 may be performed at about −20° to reflux temperature or below. Preferably, the preparation may be performed at a temperature range from about −20° C. to about 50° C. and more preferably, the preparation may be performed at a temperature range from about 10° C. to about 30° C.

The hydrochloride of the compound represented by Formula 3 may be prepared by adding anhydrous hydrochloric acid or concentrated hydrochloric acid to the compound represented by Formula 3 with use of alcohol, a mixture of alcohol and ketone, or a mixture of alcohol and ether as the solvent at a temperature range from −20° C. to reflux temperature or below.

The hydrochloride of the compound represented by Formula 3 may be prepared by adding anhydrous hydrochloric acid or concentrated hydrochloric acid to the compound represented by Formula 3 with use of alcohol, a mixture of alcohol and ketone, or a mixture of alcohol and ether as the solvent at a temperature range from −20° C. to reflux temperature or below; drying to obtain a primary acid addition salt; and then refluxing the acid addition salts in alcohol.

In the present disclosure, a preparation of compound represented by Formula 2 or the pharmaceutically acceptable salt thereof may comprise:

preparing a compound represented by Formula 6 below by reacting a compound represented by Formula 4 below with a compound represented by Formula 5 below; and deprotecting an amine protecting group from the compound represented by Formula 6.

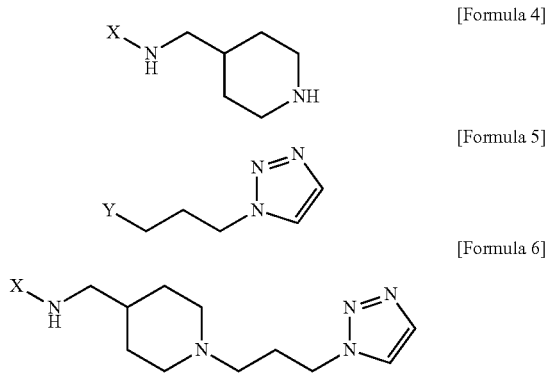

[Formula 4]

[Formula 5]

[Formula 6]

In Formulas 4 through 6,

X is the amine protecting group and Y is Cl—, Br—, I—, 4-toluenesulfonate (tosylate, $CH_3C_6H_4SO_2O$—, OTs), or methanesulfonate (mesylate, $CH_3SO_2O$—, OMs).

The preparation of the compound represented by Formula 2 or the pharmaceutically acceptable salt thereof may be represented as Scheme 2 below.

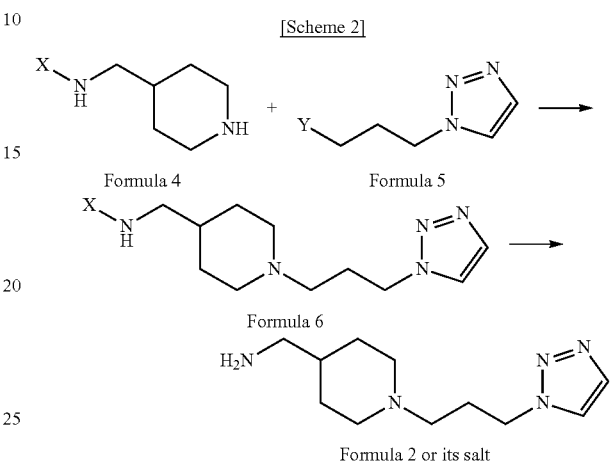

[Scheme 2]

Formula 4    Formula 5

Formula 6

Formula 2 or its salt

X and Y in Scheme 2 are same as defined in Formulas 4 to 6.

The compound represented by Formula 4 and the compound represented by Formula 5 may be synthesized via known methods or be obtained commercially.

In the present disclosure, the X performs as protecting an amine group to selectively react with —N included in piperidine ring of the compound represented by Formula 4 with the compound represented by formula 5 when preparing the compound represented by Formula 6. Types of the X are not limited if those are substances that can protect the amine group when the compound represented by Formula 4 is reacting with the compound represented by Formula 5. The X may be butoxycarbonyl (Boc) or benzyloxycarbonyl (Cbz), benzyl, 9-fluorenylmethylcarbonyl (Fmoc).

In the present disclosure, the Y may be Cl, Br, I, 4-toluenesulfonate (tosylate, $CH_3C_6H_4SO_2O$, OTs), or methanesulfonate (mesylate, $CH_3SO_2O$, OMs) and preferably, the Y may be Cl, 4-toluenesulfonate or methanesulfonate.

In the present disclosure, the reaction between the compound represented by Formula 4 and the compound represented by Formula 5 may be performed under existence of sodium iodide, potassium iodide or mixtures thereof.

In the present disclosure, the reaction of the compound represented by Formula 4 with the compound represented by Formula 5 may be performed under existence of bases. Types of the bases are not limited unless it inhibits the reaction. It may be an inorganic base, an organic base and the like, and the organic base may be a tertiary amine. For instance, the base may be sodium carbonate, sodium hydrogen carbonate, potassium carbonate, potassium hydrogen carbonate, N-methyl morpholine, isopropylethylamine, triethylamine, pyridine or mixtures thereof.

In the present disclosure, the reaction of the compound represented by Formula 4 with the compound represented by Formula 5 may be performed under both existence of one of sodium iodide, potassium iodide and mixtures thereof, and the bases.

In the present disclosure, types of solvents for the reaction between the compound represented by Formula 4 and the compound represented by Formula 5 are not limited unless it inhibits the reaction. The solvents may be acetonitrile, acetone, toluene, tetrahydrofuran, dichloromethane, N,N-dimethylformamide or mixtures thereof.

In the present disclosure, the reaction of the compound represented by Formula 4 with the compound of Formula 5 may be performed at about −20° C. to reflux temperature or below. Preferably, the reaction may be performed at a temperature range from about −20° C. to about 120° C., and more preferably the reaction may be performed at a temperature range from about 20° C. to about 90° C.

In the present disclosure, the compound represented by Formula 2 or the pharmaceutically acceptable salt thereof may be prepared by deprotecting the amine protecting group of X from the compound represented by Formula 6. That is, the compound represented by Formula 2 or the pharmaceutically acceptable salt thereof may be prepared by substituting the amine protecting group X of the compound represented by Formula 6 with hydrogen.

In the present disclosure, the reaction may be performed at about −20° C. to reflux temperature or below. Preferably, the reaction may be performed at a temperature range from about −20° C. to about 90° C., and more preferably the reaction may be performed at a temperature range from about 0° C. to about 50° C.

In the present disclosure, the deprotection of the amine protecting group X from the Formula 6 may be performed by reacting the compound represented by Formula 6 with an acid. Type of the acid are not limited if it can effectively deprotecting the amine protecting group. The acids may be trifluoroacetic acid, hydrochloric acid, acetyl chloride, trimethylsilyl chloride, sulfuric acid or mixtures thereof.

When deprotecting the X by reacting the compound represented by Formula 6 with the acid, a solvents may be dichloromethane, ethyl acetate, diethylether, $C_1$-$C_4$ linear alcohol or branched chain alcohol, or mixtures thereof.

For instance, the acid/solvent may be trifluoroacetic acid/dichloromethane, hydrochloric acid/ethyl acetate, hydrochloric acid/diethylether, hydrochloric acid/dichloromethane or hydrochloric acid/methanol when the X is butoxycarbonyl (Boc). The compound represented by Formula 2 or the pharmaceutically acceptable salt thereof may be prepared by deprotecting butoxycarbonyl from Formula 6 by using the combinations of the solvent and the acid above.

In the present disclosure, deprotection of the amine protecting group X from Formula 6 may be performed through a hydrogenation of the compound represented by Formula 6. That is, the amine protecting group X may be substituted with hydrogen by hydrogenating the compound represented by Formula 6 in the presence of a metal catalyst.

For instance, when the X is benzyloxycarbonyl (Cbz), the compound represented by Formula 2 or the pharmaceutically acceptable salt thereof may be prepared by substituting benzyloxycarbonyl, which is the amine protecting group, with hydrogen through hydrogenation of the compound represented by Formula 6 under existence of palladium/carbon.

In the present disclosure, types of the solvent for the reaction wherein the X is benzyloxycarbonyl (Cbz), are not limited unless it inhibits the reaction. The solvents may be ethyl acetate, dichloromethane, $C_1$-$C_4$ alcohol or mixtures thereof.

In the present disclosure, types of the pharmaceutically acceptable salt of the compound represented by Formula 2 are not limited, and the types are same as explained hereinbefore.

In the present disclosure, the pharmaceutically acceptable salt of the compound represented by Formula 2 may be prepared by using the conventional methods for preparing salts of a free base. The pharmaceutically acceptable salt of the compound represented by Formula 2 may be prepared by producing the salt through mixing the compound represented by Formula 2 with an acid in a proper solvent and performing the evaporation to obtain the salt; or precipitating a salt by adding an antisolvent. For instance, the salts may be prepared through preparing a solution or a suspension by adding the compound represented by Formula 2 to an inactive solvent that does not react with the compound represented by Formula 2; and then adding a desired acid thereto and conducting a concentration under reduced pressure, crystallization or other standard chemical treatments. As an example, oxalate of the compound represented by Formula 2 may be prepared by dissolving the compound represented by Formula 2 in acetone, adding oxalic acid thereto, and stirring the solution at a room temperature.

In the present disclosure, the compound represented by Formula 5 may be prepared through a method comprising:

preparing a compound represented by Formula 8 by reacting a compound represented by Formula 7 below with an azide compound; and cyclizing an azido group of the compound represented by Formula 8.

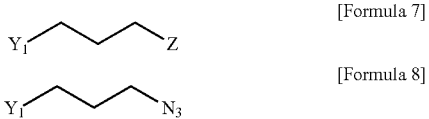

[Formula 7]

[Formula 8]

In Formulas 7 and 8, $Y_1$ and Z are independently Cl—, Br—, I—, OH—.

In the present disclosure, the $Y_1$ and Z may be identical or different. Preferably, the $Y_1$ may be Cl—, OH—, and the Z may be Br.

In the present disclosure, the compound represented by Formula 5 may be prepared via a reaction represented by Scheme 3 below.

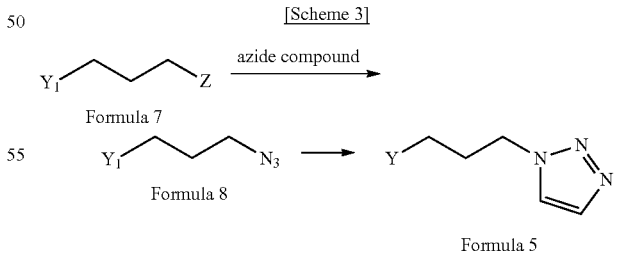

[Scheme 3]

In the present disclosure, the compound represented by Formula 8 may be prepared through substitution of one of the halogen groups of Formula 7 with the azido group via the reaction between the compound represented by Formula 7 and the azide compound. For instance, in case where $Y_1$ is Cl and Z is Br or I in the compound represented by formula 7, the compound represented by Formula 8 may be prepared through substitution of Br or I of the compound represented by Formula 7 with the azido group when reacting with azide compound. Furthermore, in case where $Y_1$ is OH and Z is Br or I in the compound represented by formula 7, the compound represented by Formula 8 may be prepared through substitution of Br or I of the compound represented by Formula 7 with the azido group when reacting with the azide compound.

In Scheme 3, the $Y_1$ of Formulas 7 and 8 may be identical or different to the Y of Formula 5. When the $Y_1$ of Formulas 7 and 8 is Cl—, Br— or I—, the Y also may be identically Cl—, Br— or I—. When the $Y_1$ of Formulas 7 and 8 is OH, the Y may be 4-toluenesulfonate (tosylate, $CH_3C_6H_4SO_2O$, OTs), or methanesulfonate (mesylate, $CH_3SO_2O$, OMs).

The azide compound may be sodium azide or potassium azide and preferably, it may be sodium azide.

In the present disclosure, types of a solvent for the reaction between the compound represented by Formula 7 and the azide compound are not limited unless it inhibits the reaction. The solvent may be dimethyl sulfoxide, acetonitrile, acetone, toluene, tetrahydrofuran, dichloromethane, N,N-dimethylformamide or mixtures thereof.

In the present disclosure, the reaction between the compound represented by Formula 7 and the azide compound may be performed at about −20° C. to reflux temperature or below. Preferably, the reaction may be performed at a temperature range from about −20° C. to about 80° C., and more preferably the reaction may be performed at a temperature range from about 0° C. to about 30° C.

In the present disclosure, a cyclization of the compound represented by Formula 8 may be performed by reacting the compound represented by Formula 8 with a carbide compound under existence of a catalyst.

The catalyst may be sodium ascorbate and copper iodide.

The carbide compound may be potassium carbide.

In the present disclosure, types of a solvent for the cyclization of the compound represented by Formula 8 are not limited unless it inhibits the cyclization. The solvent may be dimethyl sulfoxide, water, acetonitrile, acetone, toluene, tetrahydrofuran, dichloromethane, N,N-dimethylformamide or mixtures thereof.

In the present disclosure, the cyclization of the compound represented by Formula 8 may be performed at about −20° C. to reflux temperature or below. Preferably, the reaction may be performed at a temperature range from about −20° C. to about 50° C., and more preferably the reaction may be conducted at a temperature range from about 0° C. to about 20° C.

In the present disclosure, the $Y_1$ of Formulas 7 and 8 may be identical or different to the Y of Formula 5.

When the $Y_1$ of Formulas 7 and 8 is Cl—, Br— or I—, the Y also may be Cl—, Br— or I— identically. In this case, the compound represented by Formula 5 may be prepared through the cyclization of Formula 8.

When the $Y_1$ of Formulas 7 and 8 is OH, the Y may be 4-toluenesulfonate (tosylate, $CH_3C_6H_4SO_2O$, OTs), or methanesulfonate (mesylate, $CH_3SO_2$, OMs). For instance, when the $Y_1$ is OH, a compound represented by Formula 5-1 may be prepared through the cyclization of the compound represented by Formula 8, and then the compound represented by Formula 5 may be prepared by substituting H in —OH of Formula 5-1 with 4-toluenesulfonyl (tosyl, $CH_3C_6H_4SO_2$, Ts) or methanesulfonyl (mesyl, $CH_3SO_2$, -Ms).

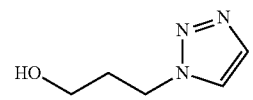

[Formula 5-1]

In this case, the compound represented by Formula 5 may be prepared through a reaction represented by Scheme 3-1 below.

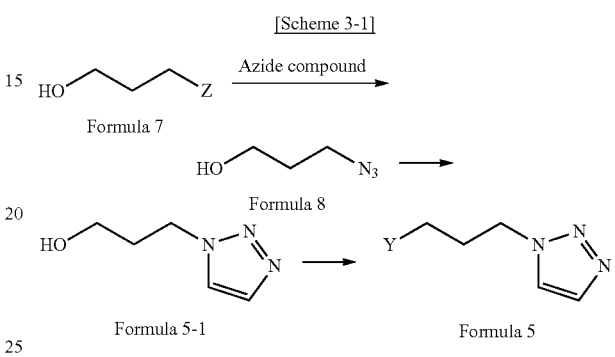

[Scheme 3-1]

Formula 7
Formula 8
Formula 5-1
Formula 5

In Scheme 3-1, the Y may be 4-toluenesulfonate (tosylate, $CH_3C_6H_4SO_2O$, OTs) or methanesulfonate (mesylate, $CH_3SO_2O$, OMs).

According to the methods of the present disclosure, the compound represented by Formula 3 or the pharmaceutically acceptable salt thereof may reduce preparation costs because the processing steps may be markedly decreased compared to the conventional methods even though using a low-priced reagent. Additionally, the purification processes may be minimized because production of related compounds and remaining related compounds may be minimized. Furthermore, the compound represented by Formula 3 or the pharmaceutically acceptable salt thereof may be prepared in high purity and yield despite the simplified process.

The present disclosure provides a compound represented by Formula 6 below, a compound represented by Formula 2 below or a pharmaceutically acceptable salt thereof.

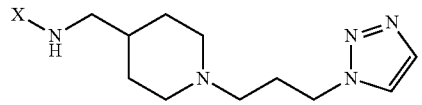

[Formula 6]

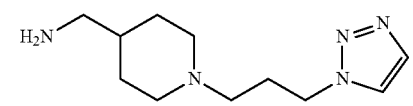

[Formula 2]

In the above Formulas, types of the X are not limited if it is a functional group that protects the amine group. It may be butoxycarbonyl (Boc) or benzyloxycarbonyl (Cbz), benzyl, 9-fluorenylmethylcarbonyl (Fmoc).

The compound represented by Formula 6, the compound represented by Formula 2 or the pharmaceutically acceptable salt thereof may be used as an intermediate for preparing a compound represented by Formula 3 or the pharmaceutically acceptable salt thereof.

[Formula 3]

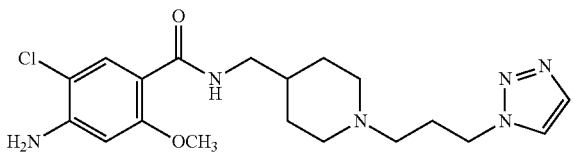

The compound represented by Formula 3 or the pharmaceutically acceptable salt thereof may be prepared in high purity and yield when preparing by using the compound represented by Formula 6, the compound represented by Formula 2 or the pharmaceutically acceptable salts thereof as the intermediate.

Also, the purification process may be minimized by reducing production of related compounds, and it is economical and proper for a large-scale production because the number of reaction processes is decreased even though using a low-priced reagent.

The compound represented by Formula 2 or the pharmaceutically acceptable salt thereof may be prepared when deprotecting the amine protecting group X from the compound represented by Formula 6. The deprotection is explained in detail hereinbefore.

In the present disclosure, types of the pharmaceutically acceptable salts of the present disclosure are not limited in its particular types, and it may be acid addition salts prepared by adding a free acid. The acid addition salts for preparing the salts may be formed by the free acid, and the free acid may be an inorganic or an organic acid. The inorganic acid may be hydrochloric acid, bromic acid, sulfuric acid or phosphoric acid; and the organic acid may be oxalic acid, adipic acid, citric acid, di-p-toluoyl-L-tartaric acid, di-p-toluoyl-D-tartaric acid, citric acid, lactic acid, maleic acid, fumaric acid, gluconic acid, methanesulfonic acid, acetic acid, glycolic acid, succinic acid, L- or D-tartaric acid, tartaric acid, 4-toluenesulfonic acid, trifluoroacetic acid, galacturonic acid, embonic acid, glutamic acid or aspartic acid. Preferably, the acid may be hydrochloric acid, oxalic acid, adipic acid, citric acid, maleic acid, fumaric acid, succinic acid, L- or D-tartaric acid or tartaric acid.

The compound represented by Formula 6, the compound represented by Formula 2, or the pharmaceutically acceptable salts thereof are as follows:
tert-butyl[[1-{3-(1H-1,2,3-triazol-1-yl)propyl}piperidin-4-yl]methyl]carbamate;
benzyl[[1-{3-(1H-1,2,3-triazol-1-yl)propyl}piperidin-4-yl]methyl]carbamate;
1-[{3-(1H-1,2,3-triazol-1-yl)propyl}piperidin-4-yl]methanamine hydrochloride;
1-[{3-(1H-1,2,3-triazol-1-yl)propyl}piperidin-4-yl]methanamine;
1-[{3-(1H-1,2,3-triazol-1-yl)propyl}piperidin-4-yl]methanamine oxalate;
1-[{3-(1H-1,2,3-triazol-1-yl)propyl}piperidin-4-yl]methanamine succinate;
1-[{3-(1H-1,2,3-triazol-1-yl)propyl}piperidin-4-yl]methanamine adipate;
1-[{3-(1H-1,2,3-triazol-1-yl)propyl}piperidin-4-yl]methanamine citrate;
1-[{3-(1H-1,2,3-triazol-1-yl)propyl}piperidin-4-yl]methanamine L-tartarate;
1-[{3-(1H-1,2,3-triazol-1-yl)propyl}piperidin-4-yl]methanamine D-tartarate;
1-[{3-(1H-1,2,3-triazol-1-yl)propyl}piperidin-4-yl]methanamine fumarate; and
1-[{3-(1H-1,2,3-triazol-1-yl)propyl}piperidin-4-yl]methanamine maleate.

The method of preparing the compound represented by Formula 6, the compound represented by Formula 2 or the pharmaceutically acceptable salts thereof are same as explained hereinbefore.

Advantageous Effect

The preparation methods of the present disclosure may be useful for mass production because a compound that could be purchased in large quantities are used and the number of reaction processes is decreased, thereby saving preparation costs and improving the yield and purity.

MODE FOR INVENTION

The present disclosure will be described more fully hereinafter with reference to the accompanying examples. However, the present disclosure may be embodied in many different forms, and should not be construed as being limited to the embodiments set forth herein. Additionally, $^1$HNMR data were measured by using a NMR 400 Spectrometer (Varian Instrument).

Example 1

Preparation of 1-(3-chloroproryl)-1H-1,2,3-triazole (Formula 5)

Step 1. Preparation of 1-azido-3-chloropropane (Formula 8)

Dimethyl sulfoxide (126 L) was added to a reaction part, and then 3-bromo-1-chloropropanol (14 kg) was added thereto at room temperature. A reaction solution was prepared by adding sodium azide (5.8 kg) thereto, washing the reaction part with dimethyl sulfoxide (14 L) and performing the stirring for 3 hours. Water (560 L) was added to the reaction solution and then was extracted with dichloromethane (420 L). An organic layer was dehydrated with anhydrous sodium sulfate (25 kg) and concentrated under reduced pressure to quantitatively obtain the titled compound as pale yellow oil (11.04 kg).
$^1$H NMR (CDCl$_3$, 400 MHz) δ3.62 (t, 2H), 3.49 (t, 2H), 2.05 (m, 2H)

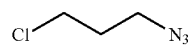

Step 2. Preparation of 1-(3-chloropropyl)-1H-1,2,3-triazole (Formula 5)

Acetonitrile (96 L) and potable water (53.0 L) were added to a reactor. 1-azido-3-chloropropane (10.6 kg) was added thereto at a room temperature. The reaction solution was prepared by adding copper iodide (8.52 kg) and sodium ascorbate (8.8 kg) thereto and then performing the stirring for 2 hours. The reaction solution was cooled to 0-10° C. Potassium carbide (9.7 kg) was slowly added to the reaction solution while not exceeding 20° C. of an internal temperature and then resulting solution was filtered using diatomite and concentrated under reduced pressure. A mixed solution was prepared by adding water (266 L) and charcoal (4.3 kg) to the concentrated residue and performing the stirring for 4 hours. The mixed solution was filtered using diatomite and extracted with dichloromethane. An organic layer was washed with 5% NaCl aqueous solution, and dehydrated and filtered by using anhydrous sodium sulfate. The filtrate was concentrated under reduced pressure to obtain the titled compound as pale yellow oil (8.86 kg; yield: 69%).

$^1$H NMR (CDCl$_3$, 400 MHz) δ 7.63 (s, 1H), 7.58 (s, 1H), 4.55 (t, 2H), 3.47 (t, 2H), 2.38 (quintet, 2H)

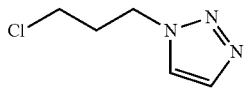

Example 2

Preparation of 3-(1H-1,2,3-triazol-1-yl) propyl methanesulfonate (Formula 5)

Step 1. Preparation of 3-azido propan-1-ol (Formula 8)

Dimethyl sulfoxide (1.3 L) was added to the reaction part, and then 3-bromo-1-propanol (0.14 kg) was added thereto at a room temperature. A reaction solution was prepared by adding sodium azide (58 g) thereto, washing the reaction part with dimethyl sulfoxide (0.2 L) and performing the stirring for 3 hours. Water (5.6 L) was added to the reaction solution and the resulting solution was extracted with dichloromethane (4.2 L). An organic layer was dehydrated with anhydrous sodium sulfate (0.5 kg) and concentrated under reduced pressure to quantitatively obtain the titled compound as oil (0.11 kg).

$^1$H NMR (CDCl$_3$, 400 MHz) δ 3.72 (m, 2H), 3.42 (m, 2H), 1.81 (m, 2H)

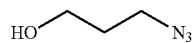

Step 2. Preparation of 3-(1H-1,2,3-triazol-1-yl)propan-1-ol (Formula 5)

Acetonitrile (303 mL) and potable water (190 mL) were added to a reaction part. 1-azido-3-chloropropane (38 g) was added thereto at a room temperature. A reaction solution was prepared by adding copper iodide (35.7 g) and sodium ascorbate (37.1 g) thereto and performing the stirring for 2 hours. The reaction solution was cooled to 0-10° C. Potassium carbide (48 g) was slowly added to the reaction solution while not exceeding 20° C. of an internal temperature. The resulting solution was filtered through diatomite and concentrated under reduced pressure. A mixed solution was prepared by adding water (950 mL) and charcoal (15 g) to the concentrated residue and performing the stirring for 4 hours. The mixed solution was filtered through diatomite and extracted with dichloromethane. An organic layer was washed with 5% NaCl aqueous solution, and dehydrated by using anhydrous sodium sulfate and filtered. The filtrate was concentrated under reduced pressure to obtain the titled compound as pale yellow oil (10 g; yield: 21%).

$^1$H NMR (DMSO d$_6$, 400 MHz) δ 8.08 (s, 1H), 7.67 (s, 1H), 4.39 (t, 2H), 3.34 (t, 2H), 1.91 (quintet, 2H)

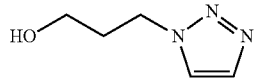

Step 3. Preparation of 3-(1H-1,2,3-triazol-1-yl) propyl methanesulfonate (Formula 5)

Dichloromethane (51 mL) was added to a reaction part, and then 3-(1H-1,2,3-triazol-1-yl)propan-1-ol (5.1 g) was added thereto. The reaction solution was cooled to 0-10° C., triethylamine (11.3 mL) was added to the reaction solution and methanesulfonyl chloride (4.7 mL) was slowly added thereto. The temperature of the resulting solution was elevated to the room temperature and then the solution was stirred for 2 hours. Potable water (102 mL) was added and then was extracted with dichloromethane (255 mL) and concentrated under reduced pressure. Potable water (75 mL) and charcoal (2.0 g) were added to the concentrated residue and stirred for 2 hours. The mixed solution was filtered through diatomite and extracted with dichloromethane (102 mL). An organic layer was washed with 5% NaCl aqueous solution, and dehydrated by using anhydrous sodium sulfate and filtered. The filtrate was concentrated under reduced pressure to obtain the titled compound as pale yellow oil (4.06 g; yield: 50%).

$^1$H NMR (CDCl$_3$, 600 MHz) δ 7.68 (s, 1H), 7.61 (s, 1H), 4.52 (t, 2H), 3.0 (s, 3H), 2.36 (quintet, 2H)

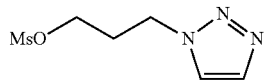 [SMILES: CS(=O)(=O)OCCCn1ccnn1]

Example 3

Preparation of 3-(1H-1,2,3-triazol-1-yl)propyl 4-methylbenzenesulfonate (Formula 5)

Dichloromethane (49 mL) was added to a reaction part, and then 3-(1H-1,2,3-triazol-1-yl)propan-1-ol (4.9 g) was added thereto. The reaction solution was cooled to 0-10° C., triethylamine (10.8 mL) was added to the reaction solution and 4-methyl benzenesulfonate (11.0 g) was slowly added thereto. The temperature of the resulting solution was elevated to a room temperature and the solution was stirred for 2 hours. Potable water (98 mL) was added to the resulting solution, and then was extracted with dichloromethane (146 mL) and concentrated under reduced pressure. Potable water (75 mL) and charcoal (2.0 g) were added to the concentrated residue and stirred for 2 hours to prepare a mixed solution. The mixed solution was filtered through diatomite and extracted with dichloromethane (200 mL). An organic layer was washed with 5% NaCl aqueous solution, and dehydrated by using anhydrous sodium sulfate and filtered. The filtrate was concentrated under reduced pressure to obtain the titled compound as oil (0.97 g; yield: 9%).

$^1$H NMR (CDCl$_3$, 600 MHz) δ 7.77 (d, 2H), 7.65 (s, 1H), 7.49 (s, 1H), 7.33 (d, 2H), 4.44 (t, 2H), 3.97 (t, 2H), 2.43 (s, 3H), 2.29 (quintet, 2H)

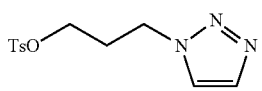 [SMILES: Cc1ccc(S(=O)(=O)OCCCn2ccnn2)cc1]

Example 4

Preparation of [1-{3-(1H-1,2,3-triazol-1-yl)propyl}piperidin-4-yl]methanamine and its hydrochloride (Formula 2) from tert-butyl(piperidin-4-ylmethyl)carbamate

Step 1. Preparation of tert-butyl[[1-{3-(1H-1,2,3-triazol-1-yl)propyl}piperidin-4-yl]methyl]carbamate (Formula 6)

Acetonitrile (1L) was added to a 2 L flask, and then tert-butyl(piperidin-4-ylmethyl)carbamate (35.2 g) was added thereto. A reaction solution was prepared by sequentially adding potassium iodide (19.1 g), calcium carbonate (227.1 g) and 1-(3-chloropropyl)-1H-1,2,3-triazole (35.9 g) thereto and performing the stirring under reflux for 7 hours. The reaction solution was cooled to a room temperature, and water (1.4 L) and 5% sodium thiosulfate solution were sequentially added to the reaction solution.

The resulting solution was extracted with dichloromethane (1.5 L), and then an organic layer was dehydrated by using magnesium sulfate and filtered. The organic layer was concentrated under reduced pressure to obtain the titled compound (88.0 g; yield: quantitative).

$^1$H NMR (400 MHz, CDCl$_3$) δ 7.68 (s, 1H), 7.55 (s, 1H), 4.59 (br s, 1H), 4.45 (t, 2H), 3.01 (t, 2H), 2.85 (d, 2H), 2.82 (t, 2H), 2.07 (m, 2H), 1.89 (m, 2H), 1.67 (d, 2H), 1.43 (s, 9H & m, 1H), 1.23 (m, 2H)

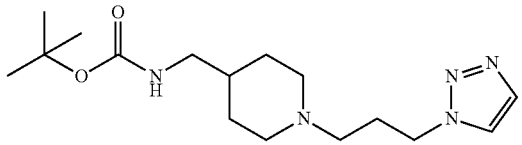 [SMILES: CC(C)(C)OC(=O)NCC1CCN(CCCn2ccnn2)CC1]

Step 2. Preparation of 1-[{3-(1H-1,2,3-triazol-1-yl)propyl}piperidin-4-yl]methanamine hydrochloride (Formula 2)

A reaction solution was prepared by dissolving tert-butyl [[1-{3-(1H-1,2,3-triazol-1-yl)propyl}piperidin-4-yl]methyl]carbamate (16.5 g) in methanol (83 mL) and performing the stirring at a room temperature for 7 hours. 2N hydrochloric acid diethyl ether (124 mL) was added to the reaction solution and stirred for 30 minutes. The resulting solution was filtered and dried under reduced pressure to obtain the titled compound (14.9 g; yield: quantitative).

$^1$H NMR (400 MHz, DMSO-d6) δ 8.20 (s, 1H), 8.17 (br s, 4H), 7.76 (s, 1H), 4.49 (t, 2H), 3.46 (d, 2H), 2.99 (m, 2H), 2.86 (m, 2H), 2.68 (m, 2H), 2.33 (m, 2H), 1.84-1.92 (m, 3H), 1.58 (m, 2H)

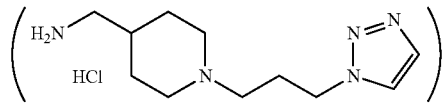

Step 3. Preparation of 1-[{3-(1H-1,2,3-triazol-1-yl)propyl}piperidin-4-yl]methanamine (Formula 2)

A reaction solution was prepared by dissolving 1-[{3-(1H-1,2,3-triazol-1-yl)propyl}piperidin-4-yl]methanamine hydrochloride (5.0 g) in water (50 mL) and pH of the reaction solution was adjusted to about 10 using 2N sodium hydroxide. The reaction solution was extracted with dichloromethane/2-propanol=4/1 (volumetric ratio, 250 mL), and then dehydrated by using anhydrous magnesium sulfate and filtered. An organic layer was concentrated under reduced pressure to obtain the titled compound (3.1 g; yield: 81%).

$^1$H NMR (400 MHz, CDCl$_3$) δ 7.67 (s, 1H), 7.55 (s, 1H), 4.44 (t, 2H), 2.86 (d, 2H), 2.58 (m, 2H), 2.28 (t, 2H), 2.07 (m, 2H), 1.89 (t, 2H), 1.71 (d, 2H), 1.17-1.30 (m, 3H)

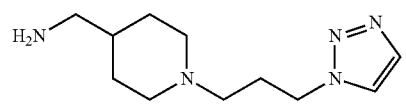

Example 5

Preparation of [1-{3-(1H-1,2,3-triazol-1-yl)propyl}piperidin-4-yl]methanamine (Formula 2) from benzyl(piperidin-4-ylmethyl)carbamate

Step 1. Preparation of benzyl[[1-{3-(1H-1,2,3-triazol-1-yl)propyl}piperidin-4-yl]methyl]carbamate (Formula 6)

A reaction solution was prepared by dissolving benzyl (piperidin-4-ylmethyl)carbamate (300 g) in acetonitrile (9 L); sequentially adding potassium iodide (201 g), calcium carbonate (1680 g) and 1-(3-chloropropyl)-1H-1,2,3-triazole (264 g) thereto; and performing the stirring under reflux for 16 hours. The reaction solution was cooled to a room temperature, and water (12 L) and 5% sodium thiosulfate solution (9 L) were sequentially added to the reaction solution. The resulting solution was extracted with dichloromethane (15 L). 2N hydrochloric acid (1.2 L) and water (12 L) were added to an organic layer, and then the layer was separated. 2N sodium hydroxide (1.8 L) was added to an aqueous layer and the resulting solution was extracted with dichloromethane (12 L). An organic layer was treated with charcoal, and then filtered and concentrated under reduced pressure. A reaction solution was prepared by adding hexane (6 L) to the concentrated residue. The reaction solution was stirred for 16 hours. The resulting solids were filtered and dried to obtain the titled compound (285 g; yield: 66%).

$^1$H NMR (400 MHz, CDCl$_3$) δ 7.66 (s, 1H), 7.52 (s, 1H), 7.34-7.28 (m, 5H), 5.07 (s, 2H), 4.44 (t, 2H), 3.08 (t, 2H), 2.83 (d, 2H), 2.28 (d, 2H), 2.08-2.01 (m, 2H), 1.90 (t, 2H), 1.67 (d, 2H), 1.46 (m, 1H), 1.26-1.17 (m, 2H)

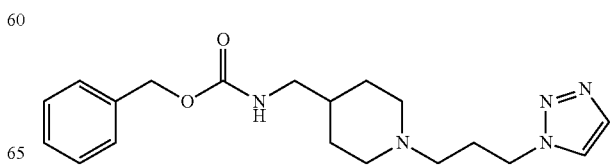

Step 2. Preparation of 1-[{3-(1H-1,2,3-triazol-1-yl) propyl}piperidin-4-yl]methanamine (Formula 2)

Benzyl[[1-{3-(1H-1,2,3-triazol-1-yl)propyl}piperidin-4-yl]methyl]carbamate (270 g) was added to a hydrogen reactor and was dissolved by adding methanol (1.35 L). A reaction solution was prepared by adding 10 wt % of palladium/carbon (containing 56 wt % of water) (61 g) to the reactor, applying a pressure with hydrogen (10 bar) thereto, and performing the stirring at 50° C. for 18 hours. The reaction solution was cooled to a room temperature and filtered through diatomite. The filtrate was concentrated under reduced pressure to obtain the titled compound (168.7 g; yield: quantitative).

$^1$H NMR (400 MHz, CDCl$_3$) δ 7.67 (s, 1H), 7.55 (s, 1H), 4.44 (t, 2H), 2.86 (d, 2H), 2.58 (m, 2H), 2.28 (t, 2H), 2.07 (m, 2H), 1.89 (t, 2H), 1.71 (d, 2H), 1.17-1.30 (m, 3H)

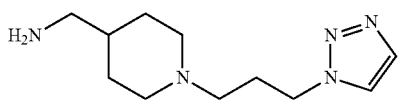

Example 6

Preparation of 1-[{3-(1H-1,2,3-triazol-1-yl) propyl}piperidin-4-yl]methanamine oxalate (Formula 2)

A solution prepared by adding oxalic acid dihydrate (0.57 g) to acetone (10 mL) was slowly added into a solution, which was prepared by dissolving 1-[{3-(1H-1,2,3-triazol-1-yl)propyl}piperidin-4-yl]methanamine (1.0 g) in acetone (10 mL) to prepare a reaction solution. The reaction solution was stirred for 4 hours, and then the resulting solids were filtered and dried to obtain the titled compound (1.30 g; yield: 93%).

$^1$H NMR (400 MHz, DMSO-d6) δ 8.11 (s, 1H), 7.71 (s, 1H), 4.39 (t, 2H), 2.90 (d, 2H), 2.68 (d, 2H), 2.49 (s, 4H), 2.21 (t, 2H), 1.98 (m, 2H), 1.82 (t, 2H), 1.66 (d, 2H), 1.46 (m, 1H), 1.18-1.09 (m, 2H)

Example 7

Preparation of 1-[{3-(1H-1,2,3-triazol-1-yl) propyl}piperidin-4-yl]methanamine succinate (Formula 2)

A solution prepared by adding succinic acid (0.53 g) into ethanol (20 mL) was slowly added into a solution, which was prepared by dissolving 1-[{3-(1H-1,2,3-triazol-1-yl) propyl}piperidin-4-yl]methanamine (1.0 g) in ethanol (10 mL) to prepare a reaction solution. The reaction solution was stirred for 4 hours and cooled to around 0° C., and then diethylether (60 mL) was added thereto. The resulting solution was further stirred for 16 hours. The resulting solids were filtered and dried to obtain the titled compound (1.44 g; yield: 94%).

$^1$H NMR (400 MHz, DMSO-d6) δ 8.11 (s, 1H), 7.71 (s, 1H), 4.39 (t, 2H), 2.90 (d, 2H), 2.68 (d, 2H), 2.49 (s, 4H), 2.21 (t, 2H), 1.98 (m, 2H), 1.82 (t, 2H), 1.66 (d, 2H), 1.46 (m, 1H), 1.18-1.09 (m, 2H)

Example 8

Preparation of 1-[{3-(1H-1,2,3-triazol-1-yl) propyl}piperidin-4-yl]methanamine adipate (Formula 2)

A solution prepared by adding adipic acid (0.65 g) to ethanol (20 mL) was slowly added into a solution which was prepared by dissolving 1-[{3-(1H-1,2,3-triazol-1-yl) propyl}piperidin-4-yl]methanamine (1.0 g) in ethanol (10 mL) to prepare a reaction solution. The reaction solution was stirred for 4 hours and cooled to around 0° C., and then diethylether (60 mL) was added thereto. The resulting solution was further stirred for 16 hours. The resulting solids were filtered and dried to obtain the titled compound (1.39 g; yield: 84%).

$^1$H NMR (400 MHz, DMSO-d6) δ 8.10 (s, 1H), 7.69 (s, 1H), 4.38 (t, 2H), 2.80 (d, 2H), 2.52-2.49 (m, 2H), 2.20-2.12 (m, 6H), 1.97 (m, 2H), 1.80 (t, 2H), 1.66 (d, 2H), 1.46 (m, 4H), 1.33 (m, 1H), 1.13-1.05 (m, 2H)

Example 9

Preparation of 1-[{3-(1H-1,2,3-triazol-1-yl) propyl}piperidin-4-yl]methanamine citrate (Formula 8)

A solution prepared by adding citric acid (0.94 g) to acetone (10 mL) was slowly added into a solution which was prepared by dissolving 1-[{3-(1H-1,2,3-triazol-1-yl) propyl}piperidin-4-yl]methanamine (1.0 g) in acetone (10 mL) to prepare a reaction solution. The reaction solution was stirred for 4 hours, and then the resulting solids were filtered and dried to obtain the titled compound (1.59 g; yield: 86%).

$^1$H NMR (400 MHz, DMSO-d6) δ 8.10 (s, 1H), 7.71 (s, 1H), 4.39 (t, 2H), 2.89 (d, 2H), 2.69 (d, 2H), 2.56-2.45 (m, 4H), 2.29-2.27 (m, 2H), 2.01-1.88 (m, 6H), 1.68 (d, 2H), 1.52-1.51 (m, 1H), 1.22-1.14 (m, 2H)

Example 10

Preparation of 1-[{3-(1H-1,2,3-trizol-1-yl) propyl}piperidin-4-yl]methanamine L-tartrate (Formula 2)

A solution prepared adding L-tartaric acid (0.67 g) to ethanol (10 mL) was slowly added to a solution which was prepared by dissolving 1-[{3-(1H-1,2,3-trizol-1-yl) propyl}piperidin-4-yl]methanamine (1.0 g) in ethanol (10 mL), and then diethylether (40 mL) was added to prepare a reaction solution. The reaction solution was stirred for 4 hours, and then the resulting solids were filtered and dried to obtain the titled compound (1.64 g; yield: 98%).

$^1$H NMR (400 MHz, DMSO-d6) δ 8.10 (s, 1H), 7.70 (s, 1H), 4.39 (t, 2H), 3.89 (s, 2H), 2.87 (d, 2H), 2.68 (d, 2H), 2.28 (t, 2H), 2.00-1.85 (m, 4H), 1.68 (d, 2H), 1.53 (m, 1H), 1.21-1.13 (m, 2H)

Example 11

Preparation of 1-[{3-(1H-1,2,3-trizol-1-yl) propyl}piperidin-4-yl]methanamine D-tartrate (Formula 2)

A solution prepared by adding D-tartaric acid (0.67 g) to ethanol (10 mL) was slowly added to a solution which was prepared by dissolving 1-[{3-(1H-1,2,3-trizol-1-yl)

propyl}piperidin-4-yl]methanamine (1.0 g) in ethanol (10 mL), and then diethylether (40 mL) was added to prepare a reaction solution. The reaction solution was stirred for 4 hours, and then the resulting solids were filtered and dried to obtain the titled compound (1.65 g; yield: 99%).

$^1$H NMR (400 MHz, DMSO-d6) δ 8.10 (s, 1H), 7.70 (s, 1H), 4.39 (t, 2H), 3.83 (s, 2H), 2.84 (d, 2H), 2.68 (d, 2H), 2.24 (t, 2H), 1.99-1.92 (m, 2H), 1.85 (t, 2H), 1.67 (d, 2H), 1.49 (m, 1H), 1.20-1.12 (m, 2H)

Example 12

Preparation of 1-[{3-(1H-1,2,3-triazol-1-yl) propyl}piperidin-4-yl]methanamine fumarate (Formula 2)

A solution prepared by adding fumaric acid (0.52 g) to ethanol (10 mL) was slowly added to a solution which was prepared by dissolving 1-[{3-(1H-1,2,3-trizol-1-yl) propyl}piperidin-4-yl]methanamine (1.0 g) in ethanol (10 mL), and then diethylether (40 mL) was added to prepare a reaction solution. The reaction solution was stirred for 4 hours, and then the resulting solids were filtered and dried to obtain the titled compound (1.49 g; yield: 98%).

$^1$H NMR (400 MHz, DMSO-d6) δ 8.10 (s, 1H), 7.70 (s, 1H), 6.44 (s, 2H), 4.38 (t, 2H), 2.83 (d, 2H), 2.66 (d, 2H), 2.24 (t, 2H), 1.99-1.92 (m, 2H), 1.85 (t, 2H), 1.68 (d, 2H), 1.50 (m, 1H), 1.19-1.11 (m, 2H)

Example 13

Preparation of 1-[{3-(1H-1,2,3-triazol-1-yl) propyl}piperidin-4-yl]methanamine maleate (Formula 2)

A solution prepared by adding maleic acid (0.52 g) to ethanol (10 mL) was slowly added to a solution which was prepared by dissolving 1-[{3-(1H-1,2,3-trizol-1-yl) propyl}piperidin-4-yl]methanamine (1.0 g) in ethanol (10 mL), and then diethylether (40 mL) was added to prepare a reaction solution. The reaction solution was stirred for 4 hours, and then the resulting solids were filtered and dried to obtain the titled compound (0.96 g; yield: 63%).

$^1$H NMR (400 MHz, DMSO-d6) δ 8.15 (s, 1H), 7.76 (s, 1H), 6.02 (s, 2H), 4.48 (t, 2H), 2.96 (bs, 2H), 2.74 (bs, 2H), 2.24 (m, 2H), 1.88-1.84 (m, 2H), 1.85 (t, 2H), 1.68 (d, 2H), 1.50 (m, 1H), 1.19-1.11 (m, 2H)

Example 14

Preparation of N-[[1-{3-(1,2,3-triazol-1-yl) propyl}piperidin-4-yl]methyl]-4-amino-5-chloro-2-methoxybenzamide (Formula 3)

4-amino-5-chloro-2-methoxybenzoic acid (1.0 g) was dissolved in dichloromethane (50 mL) and cooled to 0° C. N-(3-dimethylaminopropyl)-N'-ethylcarbodiimide hydrochloride (1.14 g) and 1-hydroxybenzotriazole hydrate (0.80 g) were sequentially added to the solution and stirred for 3.5 hours. A reaction solution was prepared by sequentially adding diisopropylethylamine (3.21 g) and [1-{3-(1H-1,2,3-triazol-1-yl)propyl}piperidin-4-yl]methanamine (1.33 g) thereto and performing the stirring for 5 minutes. The temperature of the reaction solution was elevated to a room temperature. The reaction solution was further stirred for 14 hours. Water (40 mL) was added to the reaction solution and stirred for 5 minutes, and then an organic layer was separated. Dichloromethane (20 mL) was added to a aqueous layer and the organic layer was extracted again. The aqueous layer was extracted by collecting the organic layers and adding water (30 mL) and 1N hydrochloric acid (15 mL) thereto. 2N sodium hydroxide (7.5 mL) was added to the aqueous layer and stirred for 14 hours. The resulting solids were filtered and washed with water, and then was concentrated under reduced pressure at 19-22° C. for 6 hours to obtain the titled compound (1.68 g; yield: 84%).

$^1$H NMR (400 MHz, CDCl$_3$) δ 8.08 (s, 1H), 7.72 (m, 1H), 7.66 (s, 1H), 7.54 (s, 1H), 6.27 (s, 1H), 4.43 (t, 2H), 4.36 (s, 1H), 3.88 (s, 3H), 3.30 (t, 2H), 2.83 (d, 2H), 2.27 (t, 2H), 2.06 (t, 2H), 1.90 (t, 2H), 1.70 (m, 2H), 1.58 (m, 1H), 1.29 (m, 2H)

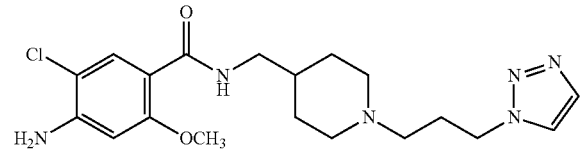

Example 15

Preparation of N-[[1-{3-(1,2,3-triazol-1-yl) propyl}piperidin-4-yl]methyl]-4-amino-5-chloro-2-methoxybenzamide (Formula 3)

4-Amino-5-chloro-2-methoxybenzoic acid (1.0 g) was dissolved in tetrahydrofuran (50 mL) and cooled to 0-5° C. Diisopropylethylamine (0.76 g) and ethyl chloroformic acid (0.64 g) were sequentially added to the solution and stirred for 1 hour. A reaction solution was prepared by sequentially adding diisopropylethylamine (2.56 g) and [1-{3-(1H-1,2,3-triazol-1-yl)propyl}piperidin-4-yl]methanamine (1.33 g) and performing the stirring for 3.5 hours. The temperature of the reaction solution was elevated and the solution was stirred under reflux. The reaction solution was further stirred for 4 hours. Water (40 mL) was added thereto and stirred for 5 minutes and an organic layer was separated. Dichloromethane (20 mL) was added to a aqueous layer and the organic layer was extracted again. The aqueous layer was extracted by collecting the organic layers and adding water (30 mL) and 1N hydrochloric acid (15 mL). 2N sodium hydroxide (7.5 mL) was added to the aqueous layer and stirred for 11 hours. The resulting solids were filtered, washed with water and then dried under reduced pressure at 19-22° C. for 24 hours to obtain the titled compound (1.28 g; yield: 63%).

$^1$H NMR (400 MHz, CDCl$_3$) δ 8.08 (s, 1H), 7.72 (m, 1H), 7.66 (s, 1H), 7.54 (s, 1H), 6.27 (s, 1H), 4.43 (t, 2H), 4.36 (s, 1H), 3.88 (s, 3H), 3.30 (t, 2H), 2.83 (d, 2H), 2.27 (t, 2H), 2.06 (t, 2H), 1.90 (t, 2H), 1.70 (m, 2H), 1.58 (m, 1H), 1.29 (m, 2H)

Example 16

Preparation of N-[[1-{3-(1,2,3-triazol-1-yl) propyl}piperidin-4-yl]methyl]-4-amino-5-chloro-2-methoxybenzamide (Formula 3)

4-Amino-5-chloro-2-methoxybenzoic acid (1.0 g) was dissolved in dichloromethane (50 mL) at 20° C. Carbonyldiimidazole (0.96 g) was added to the solution and stirred for 2.5 hours at the same temperature. A reaction solution was prepared by sequentially adding isopropylamine (2.56 g) and [1-{3-(1H-1,2,3-triazol-1-yl)propyl}piperidin-4-yl]methanamine (1.33 g) and performing the stirring for 3.5 hours, and then the temperature of the reaction solution was elevated to 40° C. The reaction solution was further stirred for 7 hours and cooled to 20° C. Water (40 mL) was added thereto. The stirring was performed for 5 minutes and an organic layer was separated. Dichloromethane (20 mL) was added to an aqueous layer and the organic layer was extracted again. The aqueous layer was extracted by collecting the organic layers and adding water (30 mL) and 1N hydrochloric acid (15 mL) thereto. 2N sodium hydroxide (7.5 mL) was added to the aqueous layer and stirred for 15 hours. The resulting solids were filtered, washed with water and dried under reduced pressure at 19-22° for 24 hours to obtain the titled compound (1.90 g; yield: 95%).

$^1$H NMR (400 MHz, CDCl$_3$) δ 8.08 (s, 1H), 7.72 (m, 1H), 7.66 (s, 1H), 7.54 (s, 1H), 6.27 (s, 1H), 4.43 (t, 2H), 4.36 (s, 1H), 3.88 (s, 3H), 3.30 (t, 2H), 2.83 (d, 2H), 2.27 (t, 2H), 2.06 (t, 2H), 1.90 (t, 2H), 1.70 (m, 2H), 1.58 (m, 1H), 1.29 (m, 2H)

Example 17

Preparation of N-[[1-{3-(1,2,3-triazol-1-yl)propyl}piperidin-4-yl]methyl]-4-amino-5-chloro-2-methoxybenzamide (Formula 3)

4-Amino-5-chloro-2-methoxybenzoic acid (0.20 g) was dissolved in dichloromethane (10 mL) and cooled to 0° C. N-methyl morpholine (0.12 g) and isobutyl chloroformate (0.16 g) were sequentially added to the solution and stirred for 3 hours. A reaction solution was prepared by sequentially adding triethylamine (0.20 g) and [1-{3-(1H-1,2,3-triazol-1-yl)propyl}piperidin-4-yl]methanamine (0.27 g) thereto, and the temperature of the reaction solution was elevated to 20° C. The stirring was performed for 14 hours, water (10 mL) was added thereto and stirred for 5 minutes, and layers were separated. Dichloromethane (10 mL) was added to an aqueous layer and an organic layer was extracted. The aqueous layer was extracted by adding water (10 mL) and 1N hydrochloric acid (3 mL) to the collected organic layers. 1N sodium hydroxide (4 mL) was added to the aqueous layer and the extraction was performed twice using a mixed solvent of dichloromethane (8 ml) and 2-propanol (2 ml). The collected organic layers were dried with sodium sulfate and filtered, and then washed with dichloromethane (10 mL). The solvent was removed by concentrating the filtered organic solution under the reduced pressure. The resulting solids were dried under reduced pressure at 19-22° C. for 18 hours to obtain the titled compound (0.41 g; yield: quantitative).

$^1$H NMR (400 MHz, CDCl$_3$) δ 8.08 (s, 1H), 7.72 (m, 1H), 7.66 (s, 1H), 7.54 (s, 1H), 6.27 (s, 1H), 4.43 (t, 2H), 4.36 (s, 1H), 3.88 (s, 3H), 3.30 (t, 2H), 2.83 (d, 2H), 2.27 (t, 2H), 2.06 (t, 2H), 1.90 (t, 2H), 1.70 (m, 2H), 1.58 (m, 1H), 1.29 (m, 2H)

Example 18

Preparation of N-[[1-{3-(1,2,3-triazol-1-yl)propyl}piperidin-4-yl]methyl]-4-amino-5-chloro-2-methoxybenzamide (Formula 3)

4-Amino-5-chloro-2-methoxybenzoic acid (0.20 g) was dissolved in dichloromethane (10 mL) and cooled to ° C. N-methyl morpholine (0.12 g) and isobutyl chloroformate (0.16 g) were sequentially added to the solution and stirred for 3 hours. A reaction solution was prepared by sequentially adding triethylamine (0.20 g) and [1-{3-(1H-1,2,3-triazol-1-yl)propyl}piperidin-4-yl]methanamine hydrochloride (0.31 g) thereto. The temperature of the reaction solution was elevated and the solution was stirred under reflux. After 4 hours of stirring, water (10 mL) was added thereto, stirred for 5 minutes and a layer was separated. Dichloromethane (10 mL) was added to an aqueous layer and an organic layer was extracted. Water (10 mL) and 1N hydrochloric acid (3 mL) were added to the collected organic layers to extract the aqueous layer. 1N sodium hydroxide (4 mL) was added to the aqueous layer, and the extraction was performed twice with a mixed solvent of dichloromethane (8 mL) and 2-propanol (2 mL). The collected organic layers were dried with sodium sulfate and filtered, and then washed with dichloromethane (10 mL). The solvent was removed by concentrating the filtered organic solution under reduced pressure. The resulting solids were dried under reduced pressure at 19-22° C. for 18 hours to obtain the titled compound (0.39 g; yield: 98%).

$^1$H NMR (400 MHz, CDCl$_3$) δ 8.08 (s, 1H), 7.72 (m, 1H), 7.66 (s, 1H), 7.54 (s, 1H), 6.27 (s, 1H), 4.43 (t, 2H), 4.36 (s, 1H), 3.88 (s, 3H), 3.30 (t, 2H), 2.83 (d, 2H), 2.27 (t, 2H), 2.06 (t, 2H), 1.90 (t, 2H), 1.70 (m, 2H), 1.58 (m, 1H), 1.29 (m, 2H)

Example 19

Preparation of N-[[1-{3-(1,2,3-triazol-1-yl)propyl}piperidin-4-yl]methyl]-4-amino-5-chloro-2-methoxybenzamide (Formula 3)

4-Amino-5-chloro-2-methoxybenzoic acid (0.2 g) was dissolved in dichloromethane (10 mL) and cooled to ° C. N-methyl morpholine (0.12 g) and isobutyl chloroformate (0.16 g) were sequentially added to the solution and stirred for 3 hours. A reaction solution was prepared by sequentially adding triethylamine (0.2 g) and [1-{3-(1H-1,2,3-triazol-1-yl)propyl}piperidin-4-yl]methanamine oxalate (0.37 g) thereto, and the temperature of the reaction solution was elevated. The reaction solution was stirred under reflux. After 4 hours of stirring, water (10 ml) was added thereto, stirred for 5 minutes, and layers were separated. Dichloromethane (10 mL) was added to an aqueous layer and an organic layer was extracted. Water (10 mL) and 1N hydrochloric acid (3 mL) were added to the collected organic layers to extract the aqueous layer. 1N sodium hydroxide (4 mL) was added to the aqueous layer and the extraction was performed twice with a mixed solvent of dichloromethane (8 mL) and 2-propanol (2 mL). The collected organic layers were dried with sodium sulfate and filtered, and then washed with dichloromethane (10 mL). The solvent was removed by concentrating the filtered organic solution under reduced pressure. The resulting solids were dried under reduced pressure at 19-22° C. for 18 hours to obtain the titled compound (0.36 g; yield: 90%).

$^1$H NMR (400 MHz, CDCl$_3$) δ 8.08 (s, 1H), 7.72 (m, 1H), 7.66 (s, 1H), 7.54 (s, 1H), 6.27 (s, 1H), 4.43 (t, 2H), 4.36 (s, 1H), 3.88 (s, 3H), 3.30 (t, 2H), 2.83 (d, 2H), 2.27 (t, 2H), 2.06 (t, 2H), 1.90 (t, 2H), 1.70 (m, 2H), 1.58 (m, 1H), 1.29 (m, 2H)

Example 20

Preparation of N-[[1-{3-(1,2,3-triazol-1-yl)propyl}piperidin-4-yl]methyl]-4-amino-5-chloro-2-methoxybenzamide (Formula 3)

4-Amino-5-chloro-2-methoxybenzoic acid (0.20 g) was dissolved in dichloromethane (10 mL) and cooled to ° C.

N-methyl morpholine (0.12 g) and isobutyl chloroformate (0.16 g) were sequentially added to the solution and stirred for 3 hours. A reaction solution was prepared by sequentially adding triethylamine (0.20 g) and [1-{3-(1H-1,2,3-triazol-1-yl)propyl}piperidin-4-yl]methanamine citrate (0.49 g) thereto. The temperature of the reaction solution was elevated and the reaction solution was stirred under reflux. After 14 hours of stirring, water (10 mL) was added thereto, stirred for 5 minutes and layers were separated. Dichloromethane (10 mL) was added to an aqueous layer and an organic layer was extracted. Water (10 mL) and 1N hydrochloric acid (3 mL) were added to the collected organic layers to extract the aqueous layer. 1N sodium hydroxide (4 mL) was added to the aqueous layer and the extraction was performed twice with a mixed solvent of dichloromethane (8 mL) and 2-propanol (2 mL). The collected organic layers were dried with sodium sulfate and filtered, and then washed with dichloromethane (10 mL). The solvent was removed by concentrating the filtered organic solution under reduced pressure. The resulting solids were dried under reduced pressure at 19-22° C. for 18 hours to obtain the titled compound (0.35 g; yield: 88%).

$^1$H NMR (400 MHz, CDCl$_3$) δ 8.08 (s, 1H), 7.72 (m, 1H), 7.66 (s, 1H), 7.54 (s, 1H), 6.27 (s, 1H), 4.43 (t, 2H), 4.36 (s, 1H), 3.88 (s, 3H), 3.30 (t, 2H), 2.83 (d, 2H), 2.27 (t, 2H), 2.06 (t, 2H), 1.90 (t, 2H), 1.70 (m, 2H), 1.58 (m, 1H), 1.29 (m, 2H)

Example 21

Preparation of N-[[1-{3-(1,2,3-triazol-1-yl)propyl}piperidin-4-yl]methyl]-4-amino-5-chloro-2-methoxybenzamide (Formula 3)

4-Amino-5-chloro-2-methoxybenzoic acid (0.20 g) was dissolved in dichloromethane (10 mL) and cooled to ° C. N-methyl morpholine (0.12 g) and isobutyl chloroformate (0.16 g) were sequentially added to the solution and stirred for 3 hours. A reaction solution was prepared by sequentially adding triethylamine (0.20 g) and [1-{3-(1H-1,2,3-triazol-1-yl)propyl}piperidin-4-yl]methanamine succinate (0.41 g) thereto. The temperature of the reaction solution was elevated and the stirring was performed under reflux. After 14 hours of stirring, water (10 mL) was added thereto, stirred for 5 minutes and layers were separated. Dichloromethane (10 mL) was added to an aqueous layer and an organic layer was extracted. Water (10 mL) and 1N hydrochloric acid (3 mL) were added to the collected organic layers to extract the aqueous layer. 1N sodium hydroxide (4 mL) was added to the aqueous layer and the extraction was performed twice with a mixed solvent of dichloromethane (8 mL) and 2-propanol (2 mL). The collected organic layers were dried with sodium sulfate and filtered, and then washed with dichloromethane (10 mL). The solvent was removed by concentrating the filtered organic solution under reduced pressure. The resulting solids were dried under reduced pressure at 19-22° C. for 18 hours to obtain the titled compound (0.36 g; yield: 90%).

$^1$H NMR (400 MHz, CDCl$_3$) δ 8.08 (s, 1H), 7.72 (m, 1H), 7.66 (s, 1H), 7.54 (s, 1H), 6.27 (s, 1H), 4.43 (t, 2H), 4.36 (s, 1H), 3.88 (s, 3H), 3.30 (t, 2H), 2.83 (d, 2H), 2.27 (t, 2H), 2.06 (t, 2H), 1.90 (t, 2H), 1.70 (m, 2H), 1.58 (m, 1H), 1.29 (m, 2H)

Example 22

Preparation of N-[[1-{3-(1,2,3-triazol-1-yl)propyl}piperidin-4-yl]methyl]-4-amino-5-chloro-2-methoxybenzamide (Formula 3)

4-Amino-5-chloro-2-methoxybenzoic acid (0.20 g) was dissolved in dichloromethane (10 mL) and cooled to ° C. N-methyl morpholine (0.12 g) and isobutyl chloroformate (0.16 g) were sequentially added to the solution and stirred for 3 hours. A reaction solution was prepared by sequentially adding triethylamine (0.20 g) and [1-{3-(1H-1,2,3-triazol-1-yl)propyl}piperidin-4-yl]methanamine L-tartrate (0.44 g) thereto. The temperature of the reaction solution was elevated and the solution was stirred under reflux. After 14 hours of stirring, water (10 mL) was added thereto, stirred for 5 minutes and layers were separated. Dichloromethane (10 mL) was added to an aqueous layer and an organic layer was extracted. Water (10 mL) and 1N hydrochloric acid (3 mL) were added to the collected organic layers to extract the aqueous layer. 1N sodium hydroxide (4 mL) was added to the aqueous layer and the extraction was performed twice with a mixed solvent of dichloromethane (8 mL) and 2-propanol (2 mL). The collected organic layers were dried with sodium sulfate and filtered, and then washed with dichloromethane (10 mL). The solvent was removed by concentrating the filtered organic solution under reduced pressure. The resulting solids were dried under reduced pressure at 19-22° C. for 18 hours to obtain the titled compound (0.40 g; yield: 100%).

$^1$H NMR (400 MHz, CDCl$_3$) 8.08 δ (s, 1H), 7.72 (m, 1H), 7.66 (s, 1H), 7.54 (s, 1H), 6.27 (s, 1H), 4.43 (t, 2H), 4.36 (s, 1H), 3.88 (s, 3H), 3.30 (t, 2H), 2.83 (d, 2H), 2.27 (t, 2H), 2.06 (t, 2H), 1.90 (t, 2H), 1.70 (m, 2H), 1.58 (m, 1H), 1.29 (m, 2H)

Example 23

Preparation of N-[[1-{3-(1,2,3-triazol-1-yl)propyl}piperidin-4-yl]methyl]-4-amino-5-chloro-2-methoxybenzamide (Formula 3)

4-Amino-5-chloro-2-methoxybenzoic acid (0.20 g) was dissolved in acetonitrile (10 mL). Carbonyldiimidazole (0.19 g) was added to the solution and stirred at 19-22° C. for 4 hours. After triethylamine (0.20 g) and [1-{3-(1H-1,2,3-triazol-1-yl)propyl}piperidin-4-yl]methanamine (0.27 g) were sequentially added thereto, the temperature of the resulting solution was elevated. Then the solution was stirred under reflux. After 21 hours of stirring, water (10 mL) was added thereto, stirred for 5 minutes, and layers were separated. Dichloromethane (10 mL) was added to an aqueous layer and an organic layer was extracted. Water (10 mL) and 1N hydrochloric acid (4 mL) were added to the collected organic layers to extract the aqueous layer. 2N sodium hydroxide (about 4 mL) was added to the aqueous layer to adjust pH of about 10. The extraction was performed twice with a mixed solvent of dichloromethane (8 mL) and 2-propanol (2 mL). The collected organic layers were dried with anhydrous magnesium sulfate and filtered, and then washed with dichloromethane (10 mL). The solvent was removed by concentrating the filtered organic solution under reduced pressure. The resulting solids were dried under reduced pressure at 19-22° C. for 17 hours to obtain the titled compound (0.41 g; yield: 100%).

$^1$H NMR (400 MHz, CDCl$_3$) δ 8.08 (s, 1H), 7.72 (m, 1H), 7.66 (s, 1H), 7.54 (s, 1H), 6.27 (s, 1H), 4.43 (t, 2H), 4.36 (s,

1H), 3.88 (s, 3H), 3.30 (t, 2H), 2.83 (d, 2H), 2.27 (t, 2H), 2.06 (t, 2H), 1.90 (t, 2H), 1.70 (m, 2H), 1.58 (m, 1H), 1.29 (m, 2H)

Example 24

Preparation of N-[[1-{3-(1,2,3-triazol-1-yl)propyl}piperidin-4-yl]methyl]-4-amino-5-chloro-2-methoxybenzamide (Formula 3)

4-Amino-5-chloro-2-methoxybenzoic acid (0.20 g) was dissolved in acetonitrile (10 mL). Carbonyldiimidazole (0.19 g) was added to the solution and stirred at 19-22° C. for 4 hours. After triethylamine (0.20 g) and [1-{3-(1H-1,2,3-triazol-1-yl)propyl}piperidin-4-yl]methanamine hydrochloride (0.31 g) were sequentially added thereto, the temperature of the resulting solution was elevated, and the solution was stirred under reflux. After 18 hours of stirring, water (10 mL) was added thereto, stirred for 5 minutes, and layers were separated. Dichloromethane (10 mL) was added to an aqueous layer and an organic layer was extracted. Water (10 mL) and 1N hydrochloric acid (4 mL) were added to the collected organic layers to extract the aqueous layer. 2N sodium hydroxide (about 4 mL) was added to the aqueous layer adjust pH of about 10. The extraction was performed twice with a mixed solvent of dichloromethane (8 mL) and 2-propanol (2 mL). The collected organic layers were dried with anhydrous magnesium sulfate and filtered and then washed with dichloromethane (10 mL). The solvent was removed by concentrating the filtered organic solution under reduced pressure. The resulting solids were dried under reduced pressure at 19-22° C. for 17 hours to obtain the titled compound (0.39 g; yield: 98%).

$^1$H NMR (400 MHz, CDCl$_3$) δ 8.08 (s, 1H), 7.72 (m, 1H), 7.66 (s, 1H), 7.54 (s, 1H), 6.27 (s, 1H), 4.43 (t, 2H), 4.36 (s, 1H), 3.88 (s, 3H), 3.30 (t, 2H), 2.83 (d, 2H), 2.27 (t, 2H), 2.06 (t, 2H), 1.90 (t, 2H), 1.70 (m, 2H), 1.58 (m, 1H), 1.29 (m, 2H)

Example 25

Preparation of N-[[1-{3-(1,2,3-triazol-1-yl)propyl}piperidin-4-yl]methyl]-4-amino-5-chloro-2-methoxybenzamide (Formula 3)

4-Amino-5-chloro-2-methoxybenzoic acid (0.20 g) was dissolved in acetonitrile (10 mL). Carbonyldiimidazole (0.19 g) was added to the solution and stirred at 19-22° C. for 4 hours. After triethylamine (0.20 g) and [1-{3-(1H-1,2,3-triazol-1-yl)propyl}piperidin-4-yl]methanamine oxalate (0.37 g) were sequentially added, the temperature of the resulting solution was elevated. Then the solution was stirred under reflux. After 21 hours of stirring, water (10 mL) was added thereto, stirred for 5 minutes, and layers were separated. Dichloromethane (10 mL) was added to an aqueous layer and an organic layer was extracted. Water (10 mL) and 1N hydrochloric acid (4 mL) were added to the collected organic layers to extract the aqueous layer. 2N sodium hydroxide (about 4 mL) was added into the aqueous layer to adjust pH of about 10. The extraction was performed twice with a mixed solvent of dichloromethane (8 mL) and 2-propanol (2 mL). The collected organic layers were dried with anhydrous magnesium sulfate and filtered, and then washed with dichloromethane (10 mL). The solvent was removed by concentrating the filtered organic solution under reduced pressure. The resulting solids were dried under reduced pressure at 19-22° C. for 17 hours to obtain the titled compound (0.25 g; yield: 63%).

1H NMR (400 MHz, CDCl$_3$) δ 8.08 (s, 1H), 7.72 (m, 1H), 7.66 (s, 1H), 7.54 (s, 1H), 6.27 (s, 1H), 4.43 (t, 2H), 4.36 (s, 1H), 3.88 (s, 3H), 3.30 (t, 2H), 2.83 (d, 2H), 2.27 (t, 2H), 2.06 (t, 2H), 1.90 (t, 2H), 1.70 (m, 2H), 1.58 (m, 1H), 1.29 (m, 2H)

Example 26

Preparation of N-[[1-{3-(1,2,3-triazol-1-yl)propyl}piperidin-4-yl]methyl]-4-amino-5-chloro-2-methoxybenzamide (Formula 3)

4-Amino-5-chloro-2-methoxybenzoic acid (0.20 g) was dissolved in acetonitrile (10 mL). Carbonyldiimidazole (0.19 g) was added to the solution and stirred at 19-22° C. for 3 hours. After triethylamine (0.20 g) and [1-{3-(1H-1,2,3-triazol-1-yl)propyl}piperidin-4-yl]methanamine citrate (0.49 g) were sequentially added thereto, the temperature of the resulting solution was elevated. Then the solution was stirred under reflux. After 16 hours of stirring, water (10 mL) was added thereto, stirred for 5 minutes, and layers were separated. Dichloromethane (10 mL) was added to an aqueous layer and an organic layer was extracted. Water (10 mL) and 1N hydrochloric acid (4 mL) were added to the collected organic layers to extract the aqueous layer. 2N sodium hydroxide (about 4 mL) was added into the aqueous layer to adjust pH of about 10. The extraction was performed twice with a mixed solvent of dichloromethane (8 mL) and 2-propanol (2 mL). The collected organic layers were dried with anhydrous magnesium sulfate and filtered, and then washed with dichloromethane (10 mL). The solvent was removed by concentrating the filtered organic solution under reduced pressure. The resulting solids were dried under reduced pressure at 19-22° for 17 hours to obtain the titled compound (0.39 g; yield: 98%).

$^1$H NMR (400 MHz, CDCl$_3$) δ 8.08 (s, 1H), 7.72 (m, 1H), 7.66 (s, 1H), 7.54 (s, 1H), 6.27 (s, 1H), 4.43 (t, 2H), 4.36 (s, 1H), 3.88 (s, 3H), 3.30 (t, 2H), 2.83 (d, 2H), 2.27 (t, 2H), 2.06 (t, 2H), 1.90 (t, 2H), 1.70 (m, 2H), 1.58 (m, 1H), 1.29 (m, 2H)

Example 27

Preparation of N-[[1-{3-(1,2,3-triazol-1-yl)propyl}piperidin-4-yl]methyl]-4-amino-5-chloro-2-methoxybenzamide (Formula 3)

4-Amino-5-chloro-2-methoxybenzoic acid (0.20 g) was dissolved in acetonitrile (10 mL). Carbonyldiimidazole (0.19 g) was added to the solution and stirred at 19-22° C. for 3 hours. After triethylamine (0.20 g) and [1-{3-(1H-1,2,3-triazol-1-yl)propyl}piperidin-4-yl]methanamine succinate (0.41 g) were sequentially added, the temperature of the resulting solution was elevated. Then the solution was stirred under reflux. After 16 hours of stirring, water (10 mL) was added thereto, stirred for 5 minutes, and layers were separated. Dichloromethane (10 mL) was added to an aqueous layer and an organic layer was extracted. Water (10 mL) and 1N hydrochloric acid (4 mL) were added to the collected organic layers to extract the aqueous layer. 2N sodium hydroxide (about 4 mL) was added into the aqueous layer to adjust pH of about 10. The extraction was performed twice with a mixed solvent of dichloromethane (8 mL) and 2-propanol (2 mL). The collected organic layers were dried with anhydrous magnesium sulfate and filtered, and then washed with dichloromethane (10 mL). The solvent was removed by concentrating the filtered organic solution under reduced pressure. The resulting solids were dried under reduced pressure at 19-22° C. for 17 hours to obtain the titled compound (0.39 g; yield: 98%).

$^1$H NMR (400 MHz, CDCl$_3$) δ 8.08 (s, 1H), 7.72 (m, 1H), 7.66 (s, 1H), 7.54 (s, 1H), 6.27 (s, 1H), 4.43 (t, 2H), 4.36 (s, 1H), 3.88 (s, 3H), 3.30 (t, 2H), 2.83 (d, 2H), 2.27 (t, 2H), 2.06 (t, 2H), 1.90 (t, 2H), 1.70 (m, 2H), 1.58 (m, 1H), 1.29 (m, 2H)

Example 28

Preparation of N-[[1-{3-(1,2,3-triazol-1-yl)propyl}piperidine-4-yl]methyl]-4-amino-5-chloro-2-methoxybenzamide (Formula 3)

4-Amino-5-chloro-2-methoxybenzoic acid (0.20 g) was dissolved in acetonitrile (10 mL). Carbonyldiimidazole (0.19 g) was added to the solution and stirred at 19-22° C. for 3 hours. After triethylamine (0.20 g) and [1-{3-(1H-1,2,3-triazol-1-yl)propyl}piperidine-4-yl]methanamine L-tartrate (0.44 g) were sequentially added thereto, the temperature of the resulting solution was elevated. Then, the solution was stirred under reflux. After 16 hours of stirring, water (10 mL) was added thereto, stirred for 5 minutes, and layers were separated. Dichloromethane (10 mL) was added to an aqueous layer and an organic layer was extracted. Water (10 mL) and 1N hydrochloric acid (4 mL) were added to the collected organic layers to extract the aqueous layer. 2N sodium hydroxide (about 4 mL) was added into the aqueous layer to adjust pH of about 10. The extraction was performed twice with a mixed solvent of dichloromethane (8 mL) and 2-propanol (2 mL). The collected organic layers were dried with anhydrous magnesium sulfate and filtered, and then washed with dichloromethane (10 mL). The solvent was removed by concentrating the filtered organic solution under reduced pressure. The resulting solids were dried under reduced pressure at 19-22° for 17 hours to obtain the titled compound (0.35 g; yield: 88%).

$^1$H NMR (400 MHz, CDCl$_3$) δ 8.08 (s, 1H), 7.72 (m, 1H), 7.66 (s, 1H), 7.54 (s, 1H), 6.27 (s, 1H), 4.43 (t, 2H), 4.36 (s, 1H), 3.88 (s, 3H), 3.30 (t, 2H), 2.83 (d, 2H), 2.27 (t, 2H), 2.06 (t, 2H), 1.90 (t, 2H), 1.70 (m, 2H), 1.58 (m, 1H), 1.29 (m, 2H)

Example 29

Preparation of N-[[1-{3-(1,2,3-triazol-1-yl)propyl}piperidin-4-yl]methyl]-4-amino-5-chloro-2-methoxybenzamide (Formula 3)

4-Amino-5-chloro-2-methoxybenzoic acid (0.20 g) was dissolved in tetrahydrofuran (10 mL). Carbonyldiimidazole (0.19 g) was added to the solution and stirred at 19-22° C. for 3 hours. After triethylamine (0.20 g) and [1-{3-(1H-1,2,3-triazol-1-yl)propyl}piperidin-4-yl]methanamine succinate (0.41 g) were sequentially added, the temperature of the resulting solution was elevated. Then, the solution was stirred under reflux. After 6 hours of stirring, water (10 mL) was added thereto, stirred for 5 minutes, and layers were separated. Dichloromethane (10 mL) was added to an aqueous layer and an organic layer was extracted. Water (10 mL) and 1N hydrochloric acid (4 mL) were added to the collected organic layers to extract the aqueous layer. 2N sodium hydroxide (about 4 mL) was added into the aqueous layer to adjust pH of about 10. The extraction was performed twice with a mixed solvent of dichloromethane (8 mL) and 2-propanol (2 mL). The collected organic layers were dried with anhydrous magnesium sulfate and filtered, and then washed with dichloromethane (10 mL). The solvent was removed by concentrating the filtered organic solution under reduced pressure. The resulting solids were dried under reduced pressure at 19-22° C. for 17 hours to obtain the titled compound (0.37 g; yield: 92.5%).

$^1$H NMR (400 MHz, CDCl$_3$) δ 8.08 (s, 1H), 7.72 (m, 1H), 7.66 (s, 1H), 7.54 (s, 1H), 6.27 (s, 1H), 4.43 (t, 2H), 4.36 (s, 1H), 3.88 (s, 3H), 3.30 (t, 2H), 2.83 (d, 2H), 2.27 (t, 2H), 2.06 (t, 2H), 1.90 (t, 2H), 1.70 (m, 2H), 1.58 (m, 1H), 1.29 (m, 2H)

Example 30

Preparation of N-[[1-{3-(1,2,3-triazol-1-yl)propyl}piperidin-4-yl]methyl]-4-amino-5-chloro-2-methoxybenzamide hydrochloride (Formula 3)

N-[[1-{3-(1,2,3-triazol-1-yl)propyl}piperidin-4-yl]methyl]-4-amino-5-chloro-2-methoxybenzamide (2.7 g) was dissolved in ethanol (13.5 mL) and methylethylketone (27 mL), and then 2N-hydrochloric acid diethyl-ether solution (4.98 mL) was slowly added thereto. The resulting solution was stirred at a room temperature for 4 hours. The resulting solids were filtered, washed with methylethylketone (13.5 mL) and dried under reduced pressure for 18 hours to obtain the titled compound (2.69 g; yield: 91%).

$^1$H NMR (400 MHz, DMSO-d6) δ 10.28 (br s, 1H), 8.19 and 8.17 (s, 1H), 8.00 (t, J=5.6 Hz, 1H), 7.75 (s, 1H), 7.64 (s, 1H), 6.67 (s, 1H), 5.95 (br s, 2H), 4.48 (t, J=6.6 Hz, 2H), 3.81 (s, 3H), 3.43 (m, 2H), 3.15 (m, 2H), 2.97 (m, 2H), 2.83 (m, 2H), 2.30 (m, 2H), 1.70-1.90 (m, 3H), 1.52 (m, 2H)

Example 31

Preparation of N-[[1-{3-(1,2,3-triazol-1-yl)propyl}piperidin-4-yl]methyl]-4-amino-5-chloro-2-methoxybenzamide hydrochloride (Formula 3)

N-[[1-{3-(1,2,3-triazol-1-yl)propyl}piperidin-4-yl]methyl]-4-amino-5-chloro-2-methoxybenzamide (2.7 g) was dissolved in ethanol (13.5 mL) and methylethylketone (27 mL), and then concentrated hydrochloric acid (35%, 0.83 mL) was added thereto. The resulting solution was stirred for 4 hours. The resulting solids were filtered, washed with methylethylketone (13.5 mL), and dried under reduced pressure for 18 hours. 2-propanol (25 mL) was added to the dried solids and refluxed for 4 hours. The solids were filtered, washed with 2-propanol (14 mL), and dried under reduced pressure for 17 hours to obtain the titled compound (2.49 g; yield: 84%).

$^1$H NMR (400 MHz, DMSO-d6) δ 10.28 (br s, 1H), 8.19 and 8.17 (s, 1H), 8.00 (t, J=5.6 Hz, 1H), 7.75 (s, 1H), 7.64 (s, 1H), 6.67 (s, 1H), 5.95 (br s, 2H), 4.48 (t, J=6.6 Hz, 2H), 3.81 (s, 3H), 3.43 (m, 2H), 3.15 (m, 2H), 2.97 (m, 2H), 2.83 (m, 2H), 2.30 (m, 2H), 1.70-1.90 (m, 3H), 1.52 (m, 2H)

Example 32

Preparation of N-[[1-{3-(1,2,3-triazol-1-yl)propyl}piperidin-4-yl]methyl]-4-amino-5-chloro-2-methoxybenzamide hydrochloride (Formula 3)

A reaction solution was prepared by dissolving N-[[1-{3-(1,2,3-triazol-1-yl)propyl}piperidin-4-yl]methyl]-4-amino- 5-chloro-2-methoxybenzamide (3.0 g) in 2-propanol (35 mL), adding concentrated hydrochloric acid (35%, 0.92 mL) thereto, and performing the stirring for 4 hours. The reaction solution was cooled to 0° C. and further stirred for 1 hour. The resulting solids were filtered. The solid was washed with 2-propanol (15 mL) and dried under reduced pressure for 16 hours to obtain the titled compound (3.08 g; yield: 94%).

$^1$H NMR (400 MHz, DMSO-d6) δ 10.28 (br s, 1H), 8.19 and 8.17 (s, 1H), 8.00 (t, J=5.6 Hz, 1H), 7.75 (s, 1H), 7.64 (s, 1H), 6.67 (s, 1H), 5.95 (br s, 2H), 4.48 (t, J=6.6 Hz, 2H), 3.81 (s, 3H), 3.43 (m, 2H), 3.15 (m, 2H), 2.97 (m, 2H), 2.83 (m, 2H), 2.30 (m, 2H), 1.70-1.90 (m, 3H), 1.52 (m, 2H)

Example 33

Preparation of N-[[1-{3-(1,2,3-triazol-1-yl)propyl}piperidin-4-yl]methyl]-4-amino-5-chloro-2-methoxybenzamide hydrochloride (Formula 3)

N-[[1-{3-(1,2,3-triazol-1-yl)propyl}piperidin-4-yl]methyl]-4-amino-5-chloro-2-methoxybenzamide (3.0 g) was dissolved in ethanol (45 mL), concentrated hydrochloric acid (35%, 0.92 mL) was added thereto. The resulting solution was stirred for 4 hours. The resulting solids were filtered. The solid was washed with ethanol (15 mL), dried under reduced pressure for 15 hours to obtain the titled compound (2.02 g; yield: 62%).

$^1$H NMR (400 MHz, DMSO-d6) δ 10.28 (br s, 1H), 8.19 and 8.17 (s, 1H), 8.00 (t, J=5.6 Hz, 1H), 7.75 (s, 1H), 7.64 (s, 1H), 6.67 (s, 1H), 5.95 (br s, 2H), 4.48 (t, J=6.6 Hz, 2H), 3.81 (s, 3H), 3.43 (m, 2H), 3.15 (m, 2H), 2.97 (m, 2H), 2.83 (m, 2H), 2.30 (m, 2H), 1.70-1.90 (m, 3H), 1.52 (m, 2H)

Example 34

Preparation of N-[[1-{3-(1,2,3-triazol-1-yl)propyl}piperidin-4-yl]methyl]-4-amino-5-chloro-2-methoxybenzamide hydrochloride (Formula 3)

N-[[1-{3-(1,2,3-triazol-1-yl)propyl}piperidin-4-yl]methyl]-4-amino-5-chloro-2-methoxybenzamide (3.0 g) was dissolved in methanol (15 mL), concentrated hydrochloric acid (35%, 0.92 mL) was added thereto. The reaction solution was stirred for 1 hour. t-butyl methyl ether (15 mL) was added to the reaction solution and further stirred for 2.5 hours. The resulting solids were filtered, washed with t-butyl methyl ether (15 mL). Then, ethanol (30 mL) was added and refluxed for 4 hours. The solids were filtered, washed with ethanol (15 mL), and dried under reduced pressure for 17 hours to obtain the titled compound (2.48 g; yield: 73%).

$^1$H NMR (400 MHz, DMSO-d6) δ 10.28 (br s, 1H), 8.19 and 8.17 (s, 1H), 8.00 (t, J=5.6 Hz, 1H), 7.75 (s, 1H), 7.64 (s, 1H), 6.67 (s, 1H), 5.95 (br s, 2H), 4.48 (t, J=6.6 Hz, 2H), 3.81 (s, 3H), 3.43 (m, 2H), 3.15 (m, 2H), 2.97 (m, 2H), 2.83 (m, 2H), 2.30 (m, 2H), 1.70-1.90 (m, 3H), 1.52 (m, 2H)

INDUSTRIAL APPLICABILITY

The preparation methods of the present disclosure can be useful for mass production because a compound that could be purchased in large quantities are used and the number of reaction processes is decreased, thereby saving preparation costs and improving the yield and purity.

What is claimed is:

1. A method for preparing a compound of Formula 3:

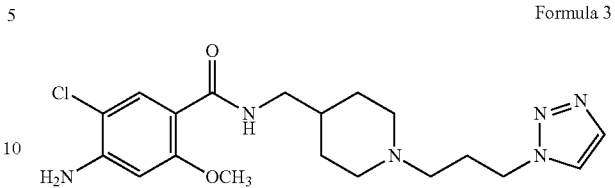

Formula 3 or a pharmaceutically acceptable salt thereof, the method comprising:
reacting a compound of Formula 1:

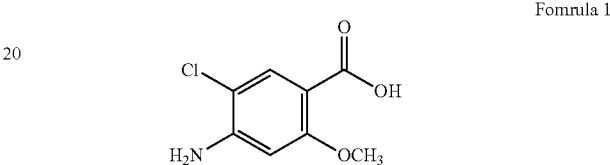

Formula 1 with a compound of Formula 2:

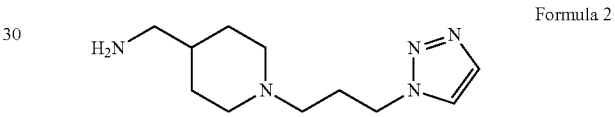

Formula 2 or a pharmaceutically acceptable salt thereof.

2. The method of claim 1, wherein the reaction of the compound of Formula 1 with the compound of Formula 2 or the pharmaceutically acceptable salt thereof is conducted in the presence of at least one compound selected from the group consisting of isobutyl chloroformate, ethyl chloroformate, carbonyldiimidazole, N-(3-dimethylaminopropyl)-N'-ethylcarbodiimide hydrochloride and 1-hydroxybenzotriazole.

3. The method of claim 1, wherein the reaction of the compound of Formula 1 with the compound of Formula 2 or the pharmaceutically acceptable salt thereof is conducted in the presence of a base.

4. The method of claim 3, wherein the base is a tertiary amine.

5. The method of claim 4, wherein the tertiary amine is at least one selected from the group consisting of N-methylmorpholine, isopropylethylamine, triethylamine and pyridine.

6. The method of claim 1, wherein the preparation of salt of the compound of Formula 3 further comprises reacting the compound of Formula 3 with an acid.

7. The method of claim 6, wherein the acid is hydrochloric acid.

8. The method of claim 6, wherein the reaction between the compound of Formula 3 and the acid is conducted in the presence of at least one solvent selected from the group consisting of an alcohol, a ketone and an ether.

9. The method of claim 6, wherein the reaction between the compound of Formula 3 and the acid is conducted in the presence of at least one solvent selected from the group consisting of a $C_1$-$C_5$ alcohol, a $C_3$-$C_{10}$ ketone and a $C_2$-$C_{10}$ ether.

10. The method of claim 1, wherein the compound of Formula 2 or the pharmaceutically acceptable salt thereof is prepared by a method comprising:

preparing a compound of Formula 6:

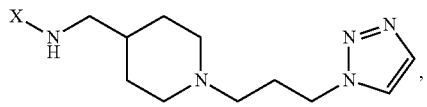

Formula 6 wherein X is an amine protecting group,
by reacting a compound of Formula 4:

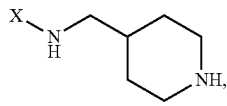

Formula 4 wherein X is an amine protecting group,
with a compound of Formula 5:

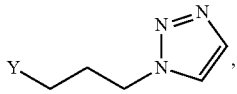

Formula 5 wherein Y is Cl, Br, I, —OTs (tosylate) or —OMs (mesylate); and
removing the protecting group X from the compound of—Formula 6—to yield a compound of Formula 2:

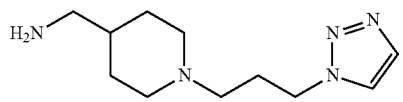 [SMILES: NCC1CCN(CCCn2ccnn2)CC1]

Formula 2 or a pharmaceutically acceptable salt thereof.

11. The method of claim 10, wherein the compound of Formula 5 is prepared by a method comprising:
preparing a compound of Formula 8:

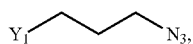

Formula 8 wherein $Y_1$ is Cl, Br, I or OH,
by reacting a compound of Formula 7:

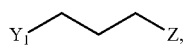

Formula 7 wherein $Y_1$ and Z each independently is Cl, Br, I or OH, with an azide compound; and
cyclizing the azido group of the compound of Formula 8.

12. The method of claim 11, wherein the cyclization of the compound of Formula 8 comprises reacting the compound of Formula 8 with a carbide compound in the presence of sodium ascorbate and copper iodide.

13. A compound of Formula 6:

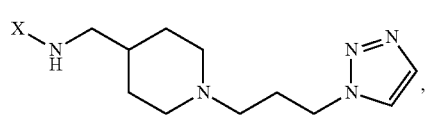

Formula 6 wherein X is an amine protecting group and the amine protecting group is butoxycarbonyl (Boc), benzyloxycarbonyl (Cbz), benzyl or 9-fluorenylmethylcarbonyl (Fmoc),
or a pharmaceutically acceptable salt thereof; or
a compound of Formula 2:

Formula 2 or a pharmaceutically acceptable salt thereof.

14. The compound of claim 13, wherein the pharmaceutically acceptable salt is hydrochloride, sulfate, phosphate, oxalate, adipate, citrate, di-p-toluoyl-L-tartarate, di-p-toluoyl-D-tartarate, citrate, lactate, maleate, fumarate, gluconate, methanesulfonate, acetate, glycolate, succinate, L- or D-tartarate, tartarate, 4-toluenesulfonate, trifluoroacetate, galacturonate, embonate, glutamate or aspartate.

15. A compound selected from the group consisting of:
1-[{3-(1H-1,2,3-triazol-1-yl)propyl}piperidin-4-yl]methanamine hydrochloride;
1-[{3-(1H-1,2,3-triazol-1-yl)propyl}piperidin-4-yl]methanamine;
1-[{3-(1H-1,2,3-triazol-1-yl)propyl}piperidin-4-yl]methanamine oxalate;
1-[{3-(1H-1,2,3-triazol-1-yl)propyl}piperidin-4-yl]methanamine succinate;
1-[{3-(1H-1,2,3-triazol-1-yl)propyl}piperidin-4-yl]methanamine adipate;
1-[{3-(1H-1,2,3-triazol-1-yl)propyl}piperidin-4-yl]methanamine citrate;
1-[{3-(1H-1,2,3-triazol-1-yl)propyl}piperidin-4-yl]methanamine L-tartarate;
1-[{3-(1H-1,2,3-triazol-1-yl)propyl}piperidin-4-yl]methanamine D-tartarate;
1-[{3-(1H-1,2,3-triazol-1-yl)propyl}piperidin-4-yl]methanamine fumarate; and
1-[{3-(1H-1,2,3-triazol-1-yl)propyl}piperidin-4-yl]methanamine maleate.

16. A method for preparing a compound of Formula 6:

Formula 6 or a pharmaceutically acceptable salt thereof, the method comprising:

reacting a compound of Formula 4:

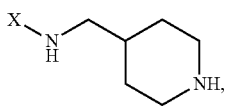
Formula 4 wherein X is an amine protecting group,
with a compound of Formula 5:

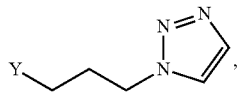
Formula 5 wherein Y is Cl, Br, I, —OTs (tosylate) or —OMs (mesylate).

17. The method of claim 16, wherein the reaction between the compound of Formula 4 and the compound of Formula 5 is conducted in the presence of at least one compound selected from the group consisting of sodium iodide and potassium iodide.

18. The method of claim 16, wherein the reaction between the compound of Formula 4 and the compound of Formula 5 is conducted in the presence of a base.

19. The method of claim 18, wherein the base is at least one selected from the group consisting of sodium carbonate, sodium hydrogen carbonate, potassium carbonate, potassium hydrogen carbonate, N-methyl morpholine, isopropylethylamine, triethylamine and pyridine.

20. A method for preparing a compound of Formula 2:

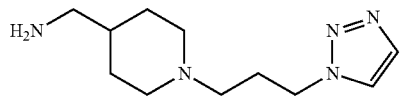 [SMILES: NCC1CCN(CCCn2ccnn2)CC1]
Formula 2 or the pharmaceutically acceptable salt thereof, the method comprising:
preparing a compound of Formula 6:

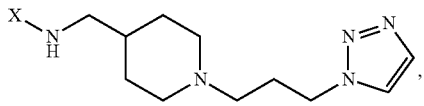
Formula 6 wherein X is an amine protecting group,
by reacting a compound of Formula 4:

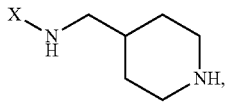
Formula 4 wherein X is an amine protecting group,
with a compound of Formula 5:

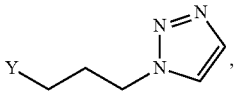
Formula 5 wherein Y is Cl, Br, I, —OTs (tosylate) or —OMs (mesylate); and
removing the amine protecting group X from the compound—of Formula 6.

21. The method of claim 20, wherein removing the amine protecting groups comprises reacting the compound of Formula 6 with an acid.

22. The method of claim 20, wherein removing the amine protecting groups comprises performing a hydrogenation of the compound of Formula 6 in the presence of palladium/carbon.

* * * * *